United States Patent
Iqbal et al.

(10) Patent No.: US 9,327,011 B2
(45) Date of Patent: *May 3, 2016

(54) NEUROTROPHIC PEPTIDES FOR THE TREATMENT OF TAUOPATHIES

(71) Applicant: Research Foundation for Mental Hygiene, Inc., Menands, NY (US)

(72) Inventors: Khalid Iqbal, Staten Island, NY (US); Inge Grundke-Iqbal, Staten Island, NY (US)

(73) Assignee: The Research Foundation For Mental Hygiene, Inc., Menands, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/464,844

(22) Filed: Aug. 21, 2014

(65) Prior Publication Data

US 2014/0357572 A1    Dec. 4, 2014

Related U.S. Application Data

(63) Continuation-in-part of application No. 14/325,880, filed on Jul. 8, 2014, which is a continuation-in-part of application No. 13/676,649, filed on Nov. 14, 2012, now Pat. No. 8,796,215, which is a continuation-in-part of application No. 13/044,323, filed on Mar. 9, 2011, now Pat. No. 8,592,374, which is a continuation-in-part of application No. 12/531,616, filed as application No. PCT/EP2008/002106 on Mar. 17, 2008, now Pat. No. 8,338,378.

(30) Foreign Application Priority Data

Mar. 16, 2007    (EP) .................................. 07450050

(51) Int. Cl.
| | | |
|---|---|---|
| *A61K 38/00* | (2006.01) | |
| *A61K 38/08* | (2006.01) | |
| *A61K 47/48* | (2006.01) | |
| *A61K 38/07* | (2006.01) | |
| *C07K 14/475* | (2006.01) | |
| *C07K 7/00* | (2006.01) | |

(52) U.S. Cl.
CPC .................. *A61K 38/08* (2013.01); *A61K 38/07* (2013.01); *A61K 47/48023* (2013.01); *C07K 7/00* (2013.01); *C07K 14/475* (2013.01)

(58) Field of Classification Search
None
See application file for complete search history.

(56) References Cited

U.S. PATENT DOCUMENTS

| | | | | |
|---|---|---|---|---|
| 8,338,378 B2 * | 12/2012 | Mossler et al. | ............... | 514/17.7 |
| 8,592,374 B2 * | 11/2013 | Mosler et al. | ................ | 514/17.7 |
| 8,796,214 B2 * | 8/2014 | Iqbal et al. | ................... | 514/17.7 |
| 8,796,215 B2 * | 8/2014 | Iqbal et al. | ................... | 514/17.8 |

* cited by examiner

*Primary Examiner* — Olga N Chernyshev
(74) *Attorney, Agent, or Firm* — David L. Nocilly; Bond Shoeneck & King, PLLC

(57) ABSTRACT

Peptide 6 and in particular, Peptide 021, may be used to treat tauopathies, such as frontotemporal dementia with Parkinsonism linked to chromosome-17 (FTDP-17) tau, corticobasal degeneration, Pick disease, progressive supranuclear palsy, Guam Parkinsonism dementia complex, dementia pugilistica also known as traumatic encephalopathy or traumatic brain injury, ceroid neuronal lipofusinosis, Hallerworden Sptaz disease, Alzheimer's disease, and adults with Down syndrome.

5 Claims, 20 Drawing Sheets

NEUROTROPHIC PEPTIDES FOR THE TREATMENT OF TAUOPATHIES

CROSS-REFERENCE TO RELATED APPLICATIONS

Figure 1:
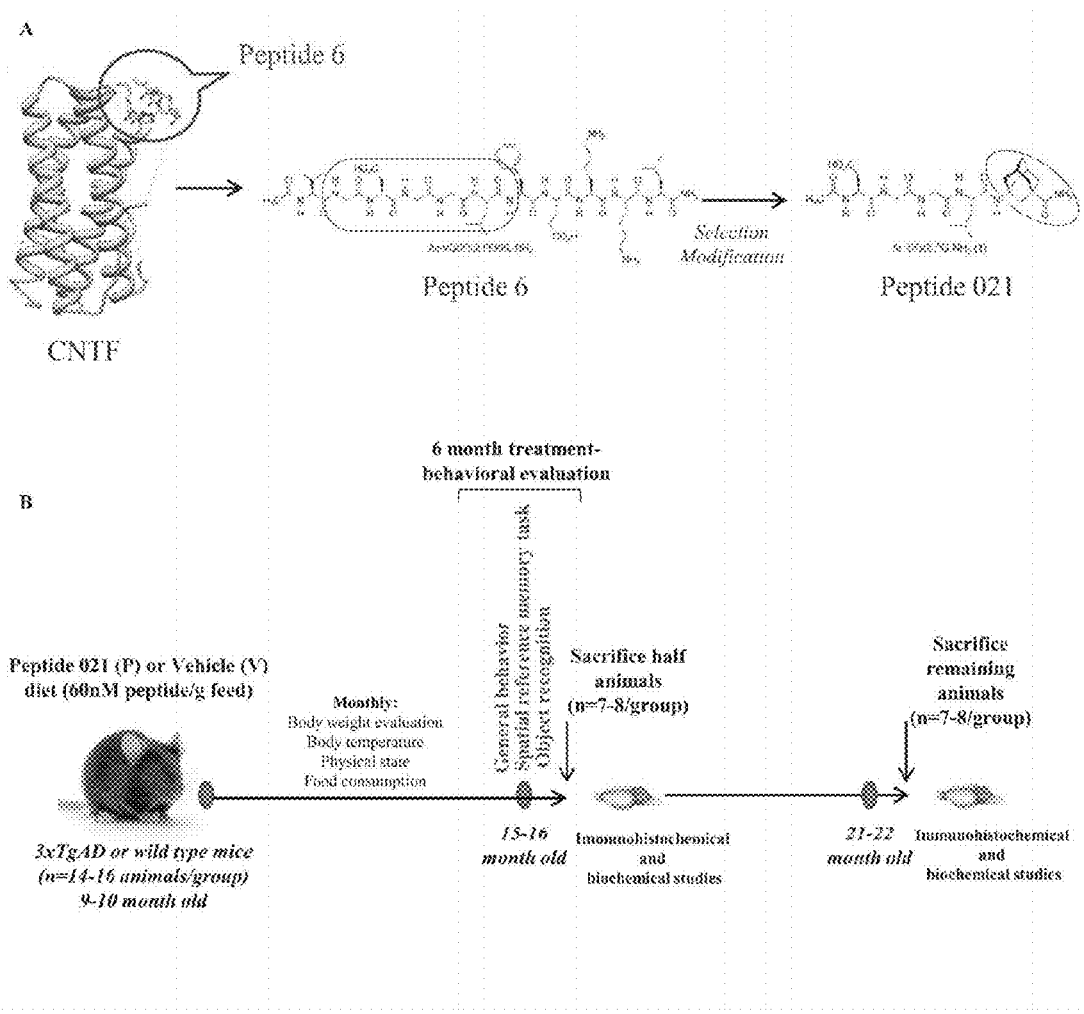

The present application is continuation-in-part of U.S. application Ser. No. 14/325,880, filed on Jul. 8, 2014, which is a continuation-in-part of U.S. Pat. No. 8,796,215, filed on Nov. 11, 2012, which is a continuation-in-part of U.S. Pat. No. 8,592,374, filed on Mar. 9, 2011, which is a continuation-in-part of U.S. Pat. No. 8,338,378, filed Sep. 16, 2009, which is a national stage application of PCT/EP2008/002106, filed on Mar. 17, 2008, which claims priority to European Application No. 07450050.5 filed Mar. 16, 2007, all of which are hereby incorporated by reference in their entireties.

The invention was supported in part by EVER NeuroPharma and a Zenith Award from Alzheimer's Association.

BACKGROUND OF THE INVENTION

1. Field of the Invention

The present invention relates to neurotrophic and/or neurogenic peptides and their use for manufacturing a medicament for the treatment of tauopathies and related neurodegenerative diseases.

2. Description of the Related Art

Tauopathies are a family of age-associated neurodegenerative diseases which are characterized histopathologically by the abnormal hyperphosphorylation and aggregation of tau in the brain, and clinically by cognitive impairment and or motor. Tauopathies include frontotemporal dementia with Parkinsonism linked to chromosome-17 (FTDP-17) tau, corticobasal degeneration, Pick disease, progressive supranuclear palsy, Guam Parkinsonism dementia complex, dementia pugilistica also known as traumatic encephalopathy or traumatic brain injury, ceroid neuronal lipofusinosis, Hallerworden Sptaz disease, Alzheimer's disease and adults with Down syndrome. The abnormal hyperphosphorylation of tau results in not only the loss of microtubule assembly promoting and stabilizing protein function, but also a gain of toxic function; the abnormally hyperphosphorylated tau sequesters normal tau as well as the other two microtubule associated proteins (MAPs), MAP1 and MAP2, and causes disruption of microtubules.

Alzheimer's disease (AD) is the most common age-dependent neurodegenerative disorder which contributes significantly to health care burden in industrialized countries, especially because of lack of an effective therapy due to its multifactorial and heterogenous nature and involvement of several different etiopathogenic mechanisms. AD is sixth most prevalent cause of mortality in U.S. and leading cause of dementia, affecting over 5 million Americans and 35 million people worldwide. The number of Americans with AD is projected to be 13.5 million by 2050 unless a drug is developed that can prevent or inhibit this disease. Histopathologically, AD is characterized by two major lesions: amyloid as diffuse and neuritic plaques composed of amyloid beta (Aβ) peptide, and neurofibrillary tangles composed of hyperphosphorylated tau protein. Currently, four FDA approved drugs (donepezil, galantamine, rivastigmine, and memantine) available for AD treatment only provide symptomatic benefit with little effect on underlying pathology. Obviously, there is impending urgency to find an effective disease-modifying therapy.

Independent of the various etiopathogenic mechanisms involved in AD, they all cause neurodegeneration. Thus, a successful therapeutic strategy for AD may include both inhibition of neurodegeneration as well as stimulation of regeneration in affected areas of the brain. This shift of balance from neurodegeneration to neural regeneration can be achieved with molecules that promote both neurogenesis and neuronal and synaptic plasticity. By virtue of their neuroprotective and neurogenic capabilities demonstrated in animal models of eurodegeneration, neurotrophic factors represent a promising therapeutic approach for AD. Many studies have shown that neurotrophic factor based approach for AD can ameliorate deficits in neurogenesis, synaptic plasticity, and cognition. However, it is unknown if this strategy could have an effect on underlying Aβ and tau pathologies.

Ciliary neurotrophic factor (CNTF) is a survival factor for various neuronal cell types. The human CNTF protein comprises 200 amino acid residues and shares significant sequence homology with CNTF proteins from other mammalian sources. The gene for human CNTF has been cloned and recombinant forms of the protein are available for clinical trials in humans. Over the past decade, a number of biological effects have been ascribed to CNTF in addition to its ability to support the survival of ciliary ganglion neurons. CNTF is believed to induce the differentiation of bipotential glial progenitor cells in the perinatal rat optic nerve and brain. Furthermore, it has been observed to promote the survival of embryonic chick dorsal root ganglion sensory neurons. In addition, CNTF supports the survival and differentiation of motor neurons, hippocampal neurons and presympathetic spinal cord neurons. The administration of CNTF to the human body has several drawbacks. While its therapeutic potential for CNS diseases is well recognized, the blood brain barrier (BBB) hinders the systemic delivery of CNTF and direct bolus injections are not suitable due to the short half-life of CNTF.

BRIEF SUMMARY OF THE INVENTION

It is therefore a principal object and advantage of the present invention to provide new medicaments comprising substances which have substantially the same or even better neurotrophic and/or neurogenic effects than CNTF. Advantageously these substances should also be able to pass the blood brain barrier in order to reach the wanted site of action in the brain.

In accordance with the foregoing objects and advantages, the present invention provides a neurotrophic and/or neurogenic peptide having an amino acid sequence selected from the group consisting of Ac-DGGL$^4$G-NH$_2$ (SEQ ID NO: 4). It has surprisingly been found that the peptides of the present invention, which are derivable from rat or human CNTF, show neurotrophic and/or neurogenic (causing growth of nerve tissue) effects which are comparable to the wild-type CNTF. Furthermore due to their small size these peptides are also able to pass the blood brain barrier and are effective for treating tauopathies.

The peptides of these polypeptides may be fused directly or via a linker to each other. Therefore, the present invention also relates to a polypeptide comprising at least two, preferably at least three, peptides of the present invention.

The peptides of the present invention may also be bound or conjugated to substances which enhance their ability to pass through the blood brain barrier.

"Fragments", as used herein, refer to parts of the peptides of the present invention, which are directly derivable from said peptides and show the same as or enhanced neurotrophic and neurogenic activities than the wild-type CNTF.

The peptides according to the present invention are preferably non immunogenic. The term "non immunogenic peptide" as used herein refers to a molecule, in particular to a peptide, which does substantially not provoke an immune response in vivo when administered to a human or an animal being. This molecule property can be determined by methods known in the art. For instance, if the administration of a molecule according to the present invention to an animal (e.g. rabbit, mouse) provokes in an animal a substantial increase of antibodies directed against said molecule, said molecule is considered as an "immunogenic peptide", if, however, substantially no molecule-specific antibodies can be induced in an animal or human upon administration of said molecule, it is considered as a "non immunogenic peptide". It is important that the peptides according to the present invention are non immunogenic because immunogenic peptides are normally eliminated from the body by the immune system.

The basic structure of the peptide according to the present invention, which is formed by amino acids, is preferably synthesised chemically according to methods known in the art, e.g. by the method developed by Merrifield et al. (Merrifield, R. B. (1963) J. Am. Chem. Soc. 85, 2149-2154; solid phase peptide synthesis).

The solid phase peptide synthesis method introduced by Merrifield in 1963, for instance, involves the attachment of a growing peptide chain to a solid support. An amino acid corresponding to the C-terminal of the target peptide is covalently attached to an insoluble polymeric support (the "resin"). The next amino acid, with a protected alpha-amino acid, is activated and reacted with the resin-bound amino acid to yield an amino-protected dipeptide on the resin. The amino-protecting group is removed and chain extension is continued with the third and subsequent protected amino acids. After the target protected peptide chain has been built up the resin is cleaved by suitable chemical means thereby releasing the crude peptide product into solution (for solid phase peptide synthesis methods and other peptide synthesis methods see also Fields, G. B. (ed.), Solid Phase Peptide Synthesis in Methods in ENZYMOLOGY, Vol. 289, Academic Press, San Diego (1997); Bodansky, M., Bodansky, A., The practice of peptide synthesis (2nd edn.), Springer Verlag, Berlin (1995); Pennington, M. W., Dunn, B. M. (eds), Peptide Synthesis Protocols, in Methods in Molecular Biology, Vol. 35, Humana Press Inc., Totowa (1994); Grant, G. A. (ed.), Synthetic peptides: a user's guide, W.H. Freemann & Co., New York (1992)).

The inorganic cation at the C-terminal end of the peptide according to the present invention may be an alkali metal or alkali earth metal cation, preferably a lithium, sodium, potassium, magnesium or calcium cation. These inorganic cations are regularly used to prepare salts of pharmaceutically active substances. The organic cation may be a quaternary ammonium ion.

If the N-terminal end of the peptide according to the present invention comprises a positive charge, said charge may be preferably compensated by an equivalent of an inorganic or organic anion. The organic anion can be, for instance, acetate anion.

Another aspect of the present invention relates to a pharmaceutical composition comprising at least one peptide according to the present invention and/or at least one peptide having an amino acid sequence selected from the group consisting of Ac-DGGL$^A$G-NH$_2$ (SEQ ID NO: 4) and optionally at least one pharmaceutically acceptable excipient and/or carrier.

The peptides according to the present invention may be formulated in a pharmaceutical preparation, which can be administered to a patient for preventing or treating a cerebral disease, in particular, a neurodegenerative disease. The pharmaceutical preparation may further comprise pharmaceutically acceptable excipients and/or carriers. Suitable excipients and carriers are well known in the art (see e.g. "Handbook of Pharmaceutical Excipients", 5th Edition by Raymond C. Rowe, Paul J. Sheskey, Sian C. Owen (2005), APhA Publications).

The composition of the present invention may further comprise at least one additional pharmaceutically active component, which is preferably consisting of Ac-DGGL$^A$G-NH$_2$ (SEQ ID NO: 4).

The pharmaceutical preparation according to the present invention may comprise, in addition to the peptide according to the present invention, further active components, which may exhibit similar properties when administered to an individual or which may cause other reactions in the treated patient.

According to the present invention, e.g., antioxidants like vitamins may be considered as further active components because antioxidants inhibit oxidation or suppress reactions promoted by oxygen, oxygen free radicals, oxygen reactive species including peroxides. Antioxidants, especially lipid-soluble antioxidants, can be absorbed into the cell membrane to neutralize oxygen radicals and thereby protect the membrane. The antioxidants useful in the present invention are preferably vitamin antioxidants that may be selected from the group consisting of all forms of Vitamin A including retinal and 3,4-didehydroretinal, all forms of carotene such as alpha-carotene, beta-carotene, gamma carotene, delta-carotene, all forms of Vitamin C (D-ascorbic acid, L-ascorbic acid), all forms of tocopherol such as Vitamin E (Alpha-tocopherol, 3,4-dihydro-2,5,7,8-tetramethyl-2-(4,8,12-trimethyltri-decyl)-2H-1-benzopyran-6-ol), beta-tocopherol, gamma-tocopherol, delta-tocopherol, tocoquinone, tocotrienol and Vitamin E esters which readily undergo hydrolysis to Vitamin E such as Vitamin E acetate and Vitamin E succinate, and pharmaceutically acceptable Vitamin E salts such as Vitamin E phosphate, prodrugs of Vitamin A, carotene, Vitamin C, and Vitamin E, pharmaceutically acceptable salts of Vitamin A, carotene, Vitamin C, and Vitamin E, and the like, and mixtures thereof.

According to another preferred embodiment of the present invention the composition is provided for intravenous, intramuscular, spinal, epidural, transdermal, intranasal, mucosal, parenteral, oral, enteral or rectal administration.

Depending on the route of administration the pharmaceutical composition according to the present invention may be formulated, for instance, as tablets, capsules, liquids, infusion and suppositories (see e.g. "Pharmaceutical Formulation Development of Compounds" by Sven Frokjaer (1999), CRC; "Handbook of Pharmaceutical Manufacturing Formulations" by Sarfaraz K. Niazi (2004), CRC).

The peptides are preferably comprised in the composition in an amount between 0.1 µg/g to 100 mg/g, preferably 1 µg/g to 80 mg/g. In any way, the effective dosages for prevention or treatment of human patients can be optimised for given patients or patient collectives according to the routine methods available for the present field.

Another aspect of the present invention relates to the use of at least one peptide with neurotrophic and/or neurogenic activity, as defined above, which may be part of a molecule consisting of a maximum of 50, preferably a maximum of 40, more preferred a maximum of 30, even more preferred a maximum of 20, amino acids, and/or at least one peptide having an amino acid sequence selected from the group consisting of consisting of Ac-DGGL$^A$G-NH$_2$ (SEQ ID NO: 4)

for the manufacture of a medicament for the treatment and/or prevention of a neurodegenerative disease.

According to the present invention all peptides disclosed herein and exhibiting neurotrophic and/or neurogenic activity may be used for manufacturing a medicament for the treatment and/or prevention of neurodegenerative diseases.

According to a preferred embodiment of the present invention the peptide is a peptide according to the present invention as defined above.

The tauopathy and related neurodegenerative disease is preferably selected from the group consisting of Alexander disease, Alper's disease, Alzheimer disease, Amyotrophic lateral sclerosis, Ataxia tel-angiectasia, Canavan disease, chronic traumatic encephalopathy, Cockayne syndrome, Corticobasal degeneration, Creutzfeldt-Jakob disease, epilepsy, fronto-lobar dementias Huntington disease, Kennedy's disease, Krabbe disease, Lewy body dementia, Machado-Joseph disease (Spinocerebellar ataxia type 3), macular degeneration, Multiple sclerosis, Multiple System Atrophy, Parkinson disease, Pelizaeus-Merzbacher Disease, Pick's disease, Primary lateral sclerosis, Refsum's disease, Sandhoff disease, Schilder's disease, Spinocerebellar ataxia, Steele-Richardson-Olszewski disease, stroke, depression and Tabes dorsalis.

Next to these preferred neurodegenerative diseases the peptide according to the present invention may also be used to treat other cerebral disorders such as autism spectrum disorder and other developmental disabilities.

In one embodiment of the invention a peptide or protein comprising or consisting of a peptide of the present invention can be employed as a drug stimulating cerebral reparative process and used for the treatment and prevention of trauma-associated cerebral lesions, including the treatment of cerebral lesions after a fracture of the cranial vault, skull base, multiple bone fractures, the treatment for the cerebral lesions in cases of intracranial trauma (e.g. posttraumatic cerebral concussion, cerebral wounds and contusion, subarachnoid, subdural and extradural haemorrhage), the treatment and prevention of traumatic shock, the treatment of the cerebral lesions associated with the impact of radiation, lowered temperature, heat and light, air pressure, electric and ultrahigh frequency current, the treatment and prevention of delayed-onset effects of skull fractures, the treatment and prevention of delayed-onset effects of intra-cranial trauma, the treatment and prevention of delayed-onset cerebral lesions induced by radiation, complications after surgical and other medical interventions.

In another embodiment of the present invention the peptides according to the present invention may be used as a drug suppressing toxic effects of the neurotrophic agents, stimulating cerebral repair processes and revealing cerebroprotective activity for the treatment and prevention of cerebral lesions after poisoning including the treatment of cerebral lesions after poisoning with therapeutic agents, medicinal and biological compounds, the treatment of the cerebral impairment with agents of non-medical origin, the treatment and prevention of delayed-onset cerebral lesions induced by poisoning with drugs and nonmedical substances.

In another embodiment of the present invention the peptides according to the present invention may be used as drug with nootropic activity and stimulating cerebral repair processes for the treatment and prevention of mental deficiencies.

In another embodiment of the present invention the peptides according to the present invention may be used for stimulating cerebral repair processes and motional activity for the treatment and prevention of paralytic disorders including the treatment and prevention of hemiplegia, the treatment and prevention of infantile cerebral paralysis, the treatment and prevention of other paralytic syndromes (quadriplegia, paraplegia, diplegia of upper extremities, monoplegia of lower extremities).

In another embodiment of the present invention the peptides according to the present invention may be used as drug stimulating cerebral repair processes with cerebroprotective activity for the treatment and prevention of cerebral impairments in case of chromosome anomalies including Downs syndrome.

In another embodiment of the present invention the peptides according to the present invention may be used as drug stimulating cerebral repair processes with cerebroprotective activity for the treatment and prevention of cerebral impairments in case of inflammatory cerebral disorders including the treatment and prevention of cerebral impairments in case of bacterial meningitis including cryptococcus meningitis in AIDS patients, the treatment and prevention of cerebral impairments in case of nonbacterial meningitis, the treatment and prevention of cerebral impairments in case of meningitis of unclear origin, the treatment and prevention of cerebral impairments in case of encephalitis, myelitis and encephalomyelitis, including cerebral toxoplasmosis in AIDS patients, for the treatment and prevention of cerebral impairments in case of intracranial abscesses, for the treatment and prevention of cerebral impairments in case of phlebitis and thrombophlebitis of intracranial venous sinus, for the treatment and prevention of sequalae after intracranial abscesses or purulent infection.

In another embodiment of the present invention the peptides according to the present invention may be used as drug stimulating cerebral repair processes with cerebroprotective and nootropic activity for the treatment and prevention of cerebral impairments in case of cerebral-vascular disorders including the treatment and prevention of cerebral impairments in case of subarachnoid haemorrhage, treatment and prevention of cerebral impairments in case of cerebral haemorrhage, the treatment and prevention of cerebral impairments in case of occlusion and Stenosis of precerebral arteries, the treatment and prevention of cerebral impairments in case of occlusion of cerebral arteries, the treatment and prevention of cerebral impairments in case of transitory cerebral ischemia, the treatment and prevention of cerebral impairments in case of other cerebral-vascular disorders (acute cerebral-vascular disorders, cerebral atherosclerosis and other generalised cerebral-vascular disorders, hypertension encephalopathy, cerebral aneurysm, cerebral arteritis and non-purulent thrombosis of intracranial venous sinus).

In another embodiment of the present invention the peptides according to the present invention may be used as drug stimulating cerebral repair processes, having cerebroprotective and nootropic activity for the treatment and prevention of alcoholic psychosis including the treatment and prevention of delirium tremens at abstinence syndrome, the treatment and prevention of alcoholic amnestic syndrome and other alcoholic dementia disorders, the treatment and prevention of pathologic alcoholic intoxication, the treatment and prevention of alcoholic paranoia and alcoholic psychosis of paranoid type.

In another embodiment of the present invention the peptides according to the present invention may be used as drug stimulating cerebral repair processes, having cerebroprotective and nootropic activity for the treatment and prevention of cerebral impairment in case of alcoholism.

In another embodiment of the present invention the peptides according to the present invention may be used as a drug suppressing toxic effects of neurotropic agents and having cerebro-protective and nootropic activity for the treatment and prevention of drug-induced psychosis including the treatment and prevention of the drug abstinence syndrome, the treatment and prevention of drug-induced paranoid and/or hallucinatory disorders, the treatment and prevention of pathologic intoxication with medical agents, the treatment and prevention of other drug-induced psychic disorders (delirium, dementia, amnestic syndrome and organic affective syndrome).

In another embodiment of the present invention the peptides according to the present invention may be used as a drug suppressing toxic effects of neurotropic agents and having cerebro-protective activity for the treatment and prevention of drug addiction including the treatment and prevention of addiction to opioid agents, the treatment and prevention of addiction to barbiturate, sedative agents and tranquillisers, the treatment and prevention of cocaine addiction, the treatment and prevention of addiction to cannabis and derivatives thereof, the treatment and prevention of addiction to amphetamine and psychostimulating agents, the treatment and prevention of addiction to hallucinogenic agents, treatment and prevention of cerebral impairments caused by drug abuse without drug addiction (abuse of alcohol, tobacco, cannabis, hallucinogens, opioids, cocaine, psychostimulating agents, antidepressants).

In another embodiment of the present invention the peptides according to the present invention may be used as an agent for treatment and prevention of psychogenic symptoms and syndromes including the treatment and prevention of psychogenic physiologic impairments, the treatment and prevention of other psychogenic symptoms and syndromes (stammering and impediments, psychogenic anorexiatics, repeated stereotype movements, inorganic sleep disorders, psychogenic diet disorders, enuresis, psychalgia), the treatment and prevention of acute stress response, the treatment and prevention of reactions induced by psychological directions.

In another embodiment of the present invention the peptides according to the present invention may be used as an agent for treatment and prevention of inorganic psychoses including the treatment and prevention of Schizophrenie disorders, the treatment and prevention of affective psychoses, the treatment and prevention of paranoid conditions, the treatment and prevention of other inorganic psychoses (psychoses of depressive and agitate types, reactive confusion, acute paranoid reactions, psychogenic paranoid psychoses) and non-differentiated psychoses including psychoses induced with cerebral impairments in AIDS patients, the treatment and prevention of infantile psychoses including infantile autism and disintegrative psychoses.

In another embodiment of the present invention the peptides according to the present invention may be used as a drug stimulating cerebral repair processes and having cerebroprotective and nootropic activity for the treatment and prevention of cerebral impairments in case of other cerebral disorders including the treatment and prevention of cerebral impairments in case of cerebral cysts, the treatment and prevention of hypoxic cerebral damage, the treatment and prevention of cerebral impairments in case of intracranial hypertension, the treatment and prevention of cerebral impairments in case of encephalopathy.

In another embodiment of the present invention the peptides according to the present invention may be used as drug stimulating cerebral repair processes and motional activity, having cerebroprotective and nootropic effects for treatment and prevention of symptoms and syndromes in case of various cerebral disorders including the treatment and prevention of cognitive disorders, memory and attention, impairments (for instance, in case of amnestic diseases, mental deficiency, inorganic psychoses, etc.), the treatment and prevention of aphasia and apraxia (for instance, in case of amnestic diseases, inorganic psychoses, cerebral impairments due to chromosome anomalies, etc.), the treatment and prevention of emotional disorders (for instance, in case of inorganic psychoses, demyelinising cerebral disorders, etc.), the treatment and prevention of psychopathologic syndrome (for instance, in case of transitional organic psychotic conditions, drug-induced psychoses, drug addiction, etc.), the treatment and prevention of asthenic-depressive syndrome (for instance, in case of inorganic psychoses, cerebral impairments due to chromosome anomalies, etc.), the treatment and prevention of delirium syndrome (for instance, in case of drug-induced psychoses and drug addiction, inorganic psychoses, etc.), the treatment and prevention of sleep disorders (for instance, in case of cerebral tumours, transitional organic psychotic conditions, etc.), for treatment and prevention of cerebral-focal syndrome (focal pathologic symptoms) (for instance, in case of cerebral impairments caused by complications of surgical or other medical intervention, demyelinising cerebral disorders, etc.), the treatment and prevention of syndrome of motor disorders (for instance, in case of cerebral tumours, cerebral impairments caused by poisoning, etc.), the treatment and prevention of peripheral neuropathy, preferably diabetic neuropathy.

According to a preferred embodiment of the present invention the medicament further comprises a pharmaceutical acceptable excipient and/or carrier as defined above.

According to another preferred embodiment of the present invention the composition further comprises at least one additional pharmaceutically active component.

The medicament is preferably provided for intravenous, intramuscular, spinal, epidural, transdermal, subcutaneous, intranasal, mucosal, parenteral, oral, enteral or rectal administration.

According to a preferred embodiment of the present invention the medicament comprises the peptide in an amount between 0.1 µg/g to 100 mg/g, preferably 1 µg/g to 80 mg/g.

It is in particular preferred to use as peptide in a medicament of the present invention a peptide having the amino acid sequence consisting of Ac-DGGL$^A$G-NH$_2$ (SEQ ID NO: 4).

Another aspect of the present invention relates to a method for preventing a break out of a neurodegenerative disease in an individual and for treating an individual suffering from a neurodegenerative disease comprising the administration of a pharmaceutical composition or of an effective amount of at least one peptide according to the present invention.

The term "effective amount" of a peptide as used herein will depend among other factors on the route of administration and physical condition of the individual to be exposed to said peptide. Methods for the determination of the effective amount are known to the skilled person.

The tauopathy and related neurodegenerative disease is preferably selected from the group consisting of Alexander disease, Alper's disease, Alzheimer disease, Arnyotrophic lateral sclerosis, Ataxia tel-angiectasia, Canavan disease, chronic traumatic encephalopathy, Cockayne syndrome, Corticobasal degeneration, Creutzfeldt-Jakob disease, epilepsy, fronto-lobar dementias, Huntington disease, Kennedy's disease, Krabbe disease, Lewy body dementia, Machado-Joseph disease (Spinocerebellar ataxia type 3), Multiple sclerosis, macular degeneration, Multiple System Atrophy, Parkinson disease, Pelizaeus-Merzbacher Disease, Pick's disease, Primary lateral sclerosis, Refsum's disease, Sandhoff disease, Schilder's disease, Spinocerebellar ataxia, Steele-Richardson-Olszewski disease, peripheral neuropathy, diabetic neuropathy, stroke, depression and Tabes dorsalis.

According to a preferred embodiment of the present invention the peptide is administered to said individual at a dose of 0.1 µg/kg to 20 mg/kg body weight, preferably 0.5 µg/kg to 10 mg/kg body weight.

Another aspect of the present invention relates to the use of at least one peptide with neurotrophic and/or neurogenic activity and/or at least one peptide having an amino acid sequence selected from the group consisting of consisting of Ac-DGGL$^A$G-NH$_2$ (SEQ ID NO: 4) for the manufacture of a medicament for improving learning memory capacities in an individual.

Another aspect of the present invention relates to the use of a molecule consisting of a maximum of 50 amino acids with neurotrophic and/or neurogenic activity comprising at least one peptide according to the present invention or consisting of Ac-DGGL$^A$G-NH$_2$ (SEQ ID NO: 4) or a fragment thereof for the manufacture of a medicament for the treatment or enhancement of motor deficiencies in an individual.

Another aspect of the present invention related to use of a at least one peptide with neurotrophic and/or neurogenic activity and/or at least one peptide having an amino acid sequence selected from the group consisting of consisting of Ac-DGGL$^A$G-NH$_2$ (SEQ ID NO: 4) for treating tauopathies. Tauopathies are age-associated neurodegenerative diseases which are characterized histopathologically by the abnormal hyperphosphorylation and aggregation of tau in the brain, and clinically by cognitive impairment and/or motor dysfunction. Tauopathies include frontotemporal dementia with Parkinsonism linked to chromosome-17 (FTDP-17), corticobasal degeneration, Pick disease, progressive supranuclear palsy, Guam Parkinsonism dementia complex, dementia pugilistica also known as chronic traumatic encephalopathy or traumatic brain injury, ceroid neuronal lipofuscinosis, Hallerworden Sptaz disease, Alzheimer's disease and adults with Down syndrome

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a series of graphs showing: (A) the design and structures of CNTF derived peptidergic compounds with the position of peptide 6 in CNTF is shown. Protein Data Base rendering of one 4-helix bundle of truncated human CNTF (Residues 2-187), generated from CNTF. Only one protein chain is shown for clarity. Residues $^{149}$GGLFEKKL$^{156}$ are shown as a tube model, while the rest of the sequence are presented as ribbon. The structures of peptides 6 and 021 are also shown. From the neurogenic undecamer Ac-VGDG-GLFEKKL-NH$_2$ (Peptide 6) (SEQ ID. NO. 1), a truncated, still neurogenic tetramer Ac-DGGL-NH$_2$ (Peptide 6c) (SEQ ID. NO. 2) was designed. Addition of an unnatural amino acid based upon adamantane to the C-terminus of this subsequence via solid phase peptide synthesis methods produced Ac-DGGL$^A$G-NH$_2$ (P021) (SEQ ID. NO. 3); and (B) shows the design of the study.

Figure 2:
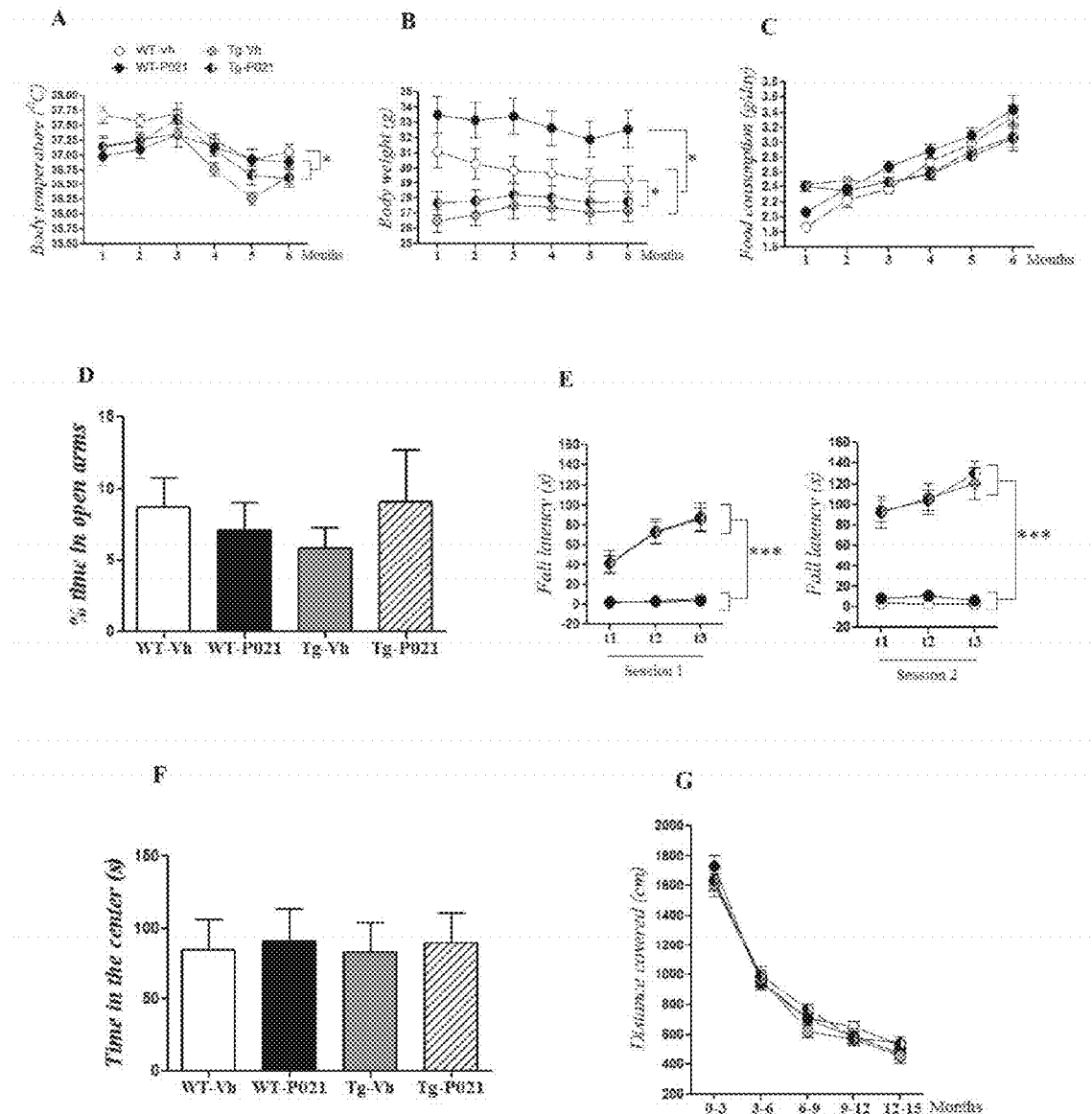

FIG. 2 is a series of graphs showing general behavioral evaluation at 15-16 months of age (6-month treatment). Treatment with Peptide 021 did not induce side effects. FIGS. 21(A-C) show monthly evaluation of body temperature, body weight, and food consumption. The WT animals treated with vehicle compared to other groups had higher body temperatures. The treatment with Peptide 021 induced an increase of weight in WT animals, and the WT mice irrespective of treatment remained heavier than 3×Tg-AD mice. The treatment with Peptide 021 did not induce any significant change of weight in 3×TgAD mice. No significant differences were found in food consumption. FIG. 2(D) shows genotype or treatment did not induce any significant difference in anxiety levels. FIG. 2(E) shows 3×TgAD mice exhibited higher scores than WT animals in the Rotarod task suggesting higher locomotivity and locomotor coordination. FIGS. 21(F-G) show that in open-field free exploration task, no significant differences were found the amount of time spent in the center of the arena and the overall distance covered suggesting comparable motivation for exploration. No effect of the treatment with Peptide 021 was observed. Data are shown as mean±S.E.M. Data based on WT-Vh (n=15), wT-P021 (n=14), Tg-Vh (n=15), and Tg-P021 (n=16). *p<0.05, p<0.01, and *p<0.001.

Figure 3:
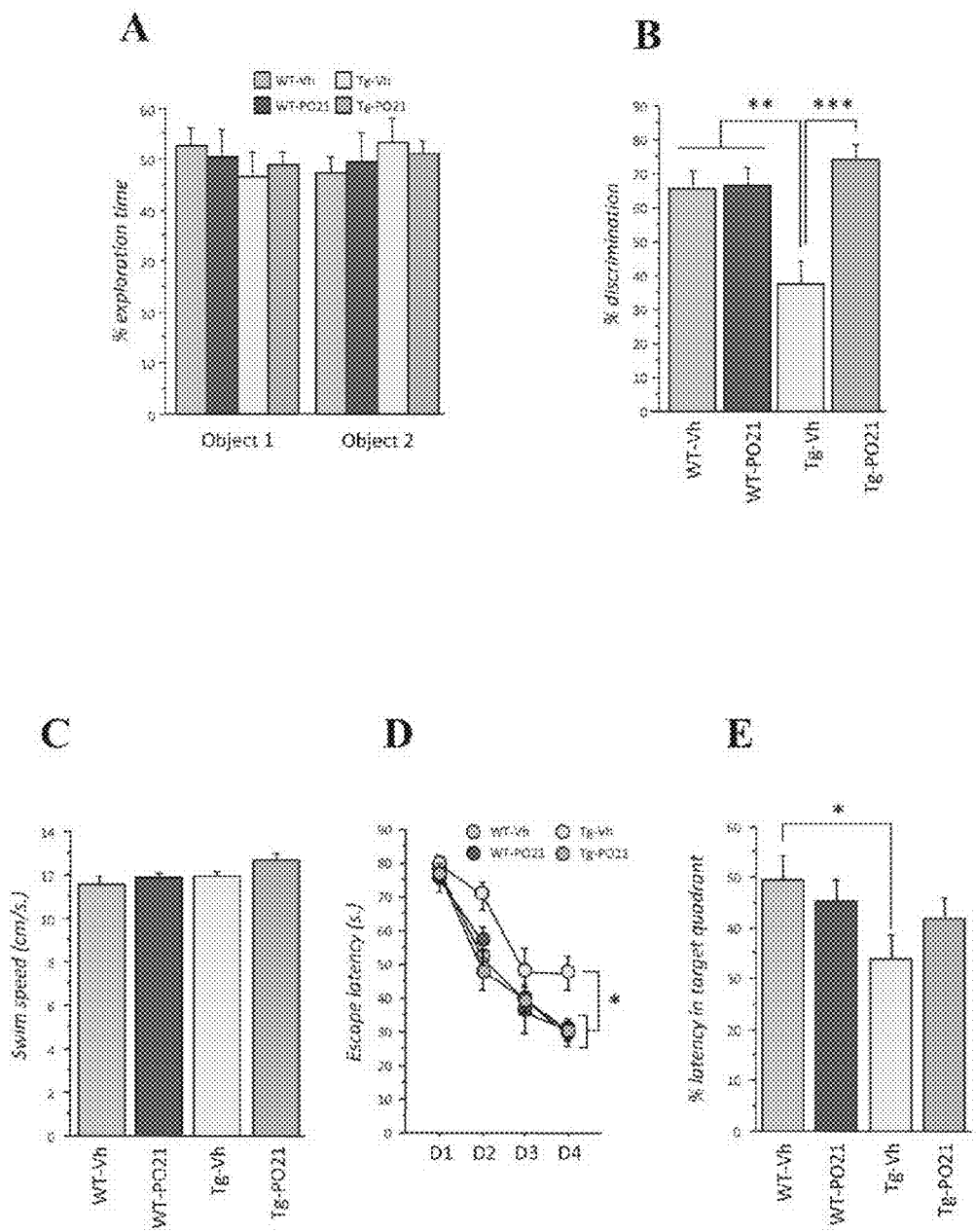

FIG. 3 is a series of graphs showing treatment with Peptide 021 rescued cognitive impairments in 15-16 months old 3×Tg-AD mice. FIGS. 22(A-C) show that in the sample phase of the one-trial object recognition task, all animal groups similarly explored both objects. In the test phase of the one-trial object recognition task, 3×Tg-AD mice explored the familiar object more (discrimination index, 0.37), reflecting an impairment of discrimination. Treatment with Peptide 021 reversed this impairment. FIGS. 22(D-E) sow that in the spatial reference memory task, 3×Tg-AD mice and WT controls displayed similar swim speed and treatment with Peptide 021 did not have any effect on velocity. During the training of the spatial reference memory task, performance of 3×Tg-AD mice was delayed compared to WT controls, but treatment with Peptide 021 reversed this impairment. In probe trial, 3×TgAD mice spent less time in the target quadrant. This deficit was rescued by treatment with Peptide 021. Data are shown as mean±S.E.M. Data based on WT-Vh (n=15), WT-P021 (n=14), Tg-Vh (n=15), and Tg-P021 (n=16). *p<0.05, p<0.01, and *p<0.001.

Figure 4:
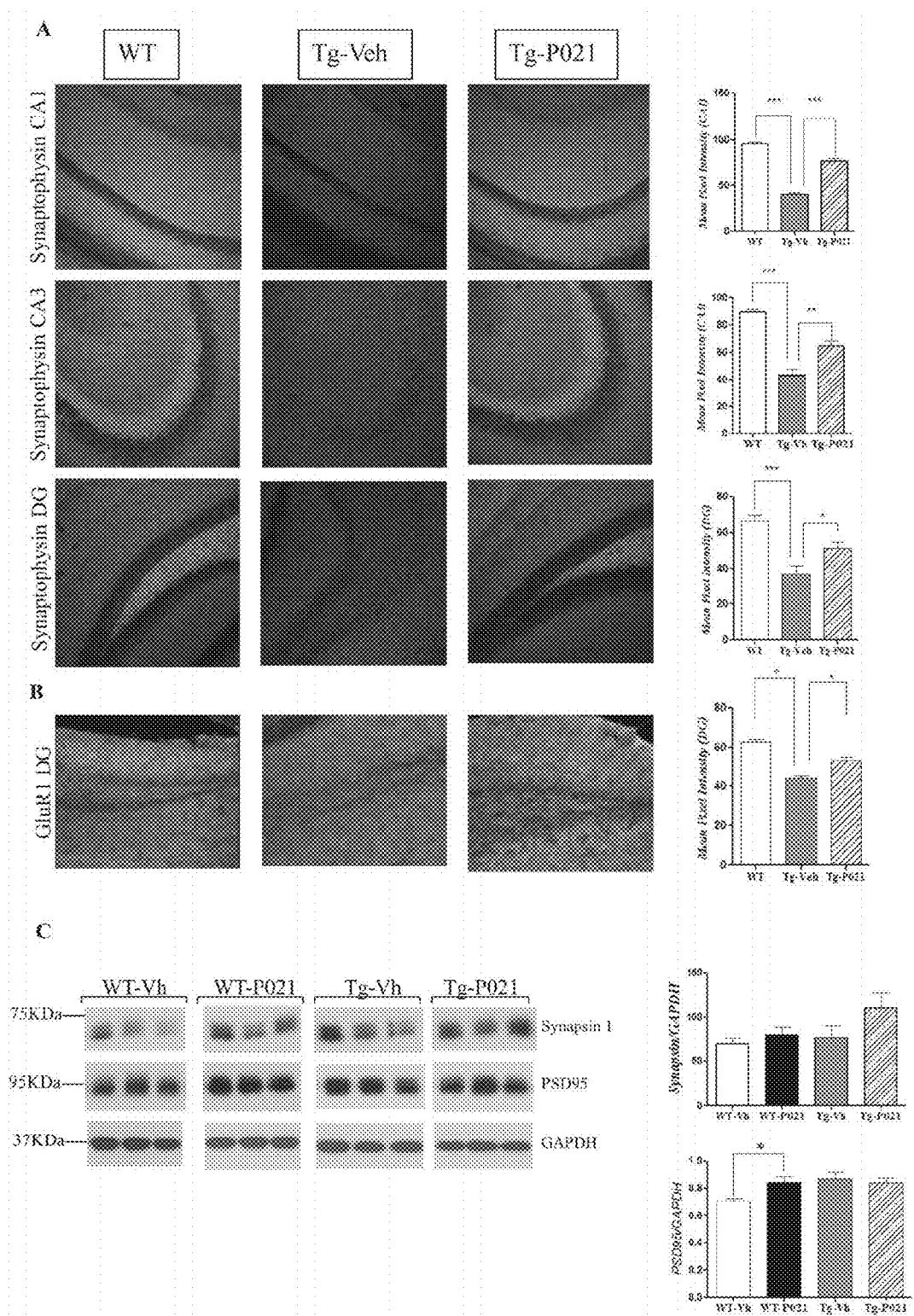

FIG. 4 is a series of graphs showing treatment with Peptide 021 prevented synaptic loss in 15-16 months old 3×TgAD mice. FIG. 4A shows that 3×TgAD mice showed significantly reduced synaptophysin density in the CA1, CA3, and dentate gyrus of the hippocampus. Treatment with Peptide 021 restored synaptophysin densities to WT control levels. Representative photomicrographs illustrating synaptophysin immunoreactivity in the different regions of hippocampus are shown. FIG. 4B shows Peptide 021 induced increase in the glutamate receptor expression (GluR1 in dentate gyrus). FIG. 4C shows Western blots developed with specific synaptic marker antibodies, synapsin 1 and PSD95. A significant increase in PSD95 expression was induced by Peptide 021 treatment in WT animals. Representative Western blots from 3 animals from each group are shown. Quantification of the Western blots is shown as mean±S.E.M. from WT-Vh (n=7), WT-P021 (n=7), Tg-Vh (n=7), and Tg-P021 (n=8). *p<0.05, p<0.01, and *p<0.001.

Figure 5:
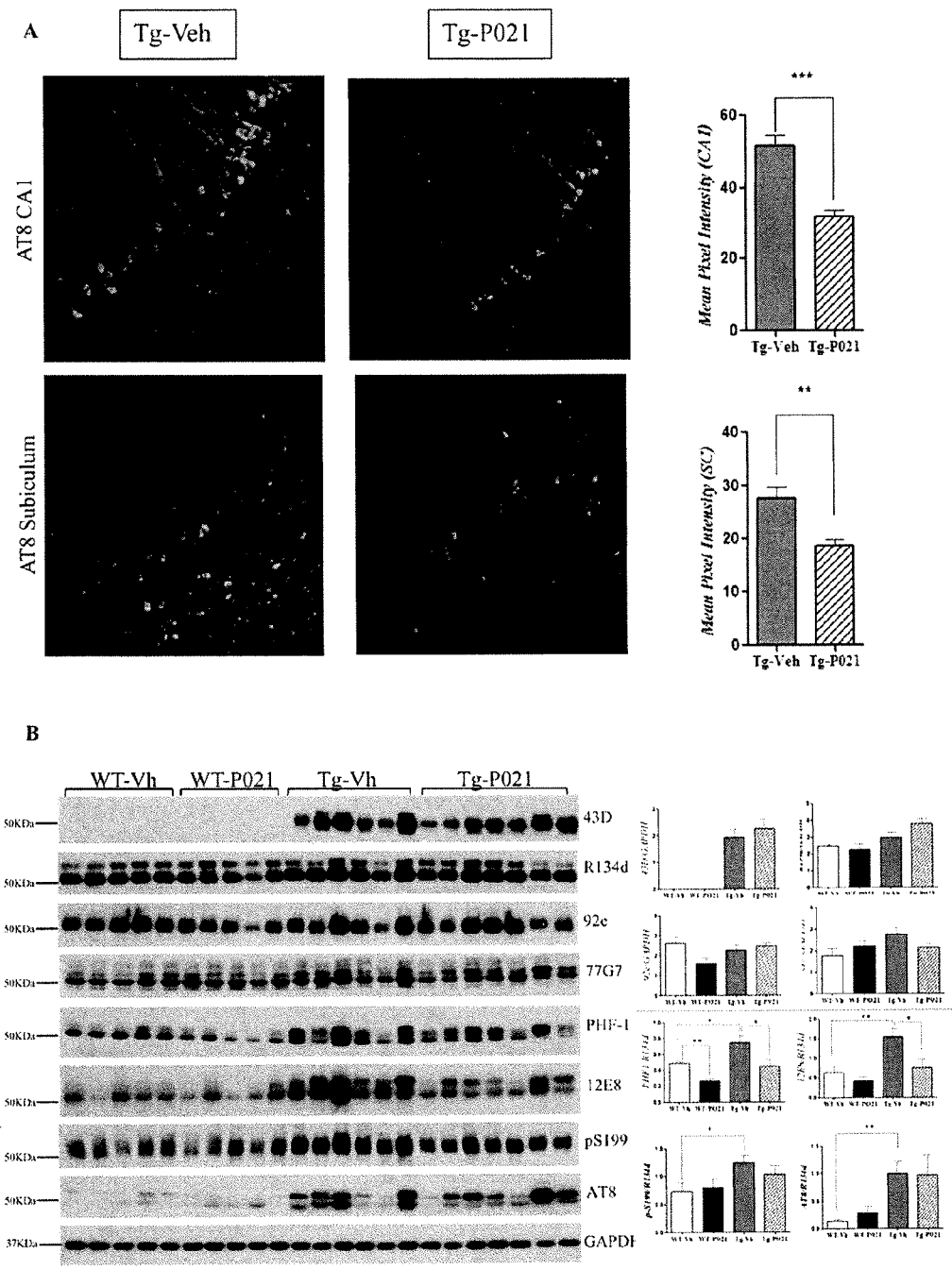

FIG. 5 is a series of graphs showing treatment with Peptide 021 significantly reduced abnormal hyperphosphorylation tau both in 15-16 months old (6 months treatment) and 21-22 months old (12 months treatment) animals. FIG. 5A shows that in the subiculum and the CA1 regions of the hippocampus, AT8 (tau pSer202, pThr 205) density was decreased by treatment with Peptide 021 in 3×Tg-AD mice. Representative photomicrographs illustrating AT8 immunoreactivity in the different regions of hippocampus are shown. FIG. 5B shows that Peptide 021 treatment significantly reduced abnormal hyperphosphorylation of tau at sites pSerine 396/pSerine 404 (PHF-1) and pSerine-262/pSerine-356 (12E8). Blots developed with human specific tau antibody 43D showed the protein expression only in 3×TgAD mice. Pan-tau antibodies, 92e, R134d, and 77G7 did not show any significant difference between groups. Quantification of the Western blots is shown as mean±S.E.M. from WT-Vh (n=5), WT-P021 (n=5), Tg-Vh (n=6), and Tg-P021 (n=7). *$p<0.05$, $p<0.01$, and *$p<0.001$.

Figure 6:
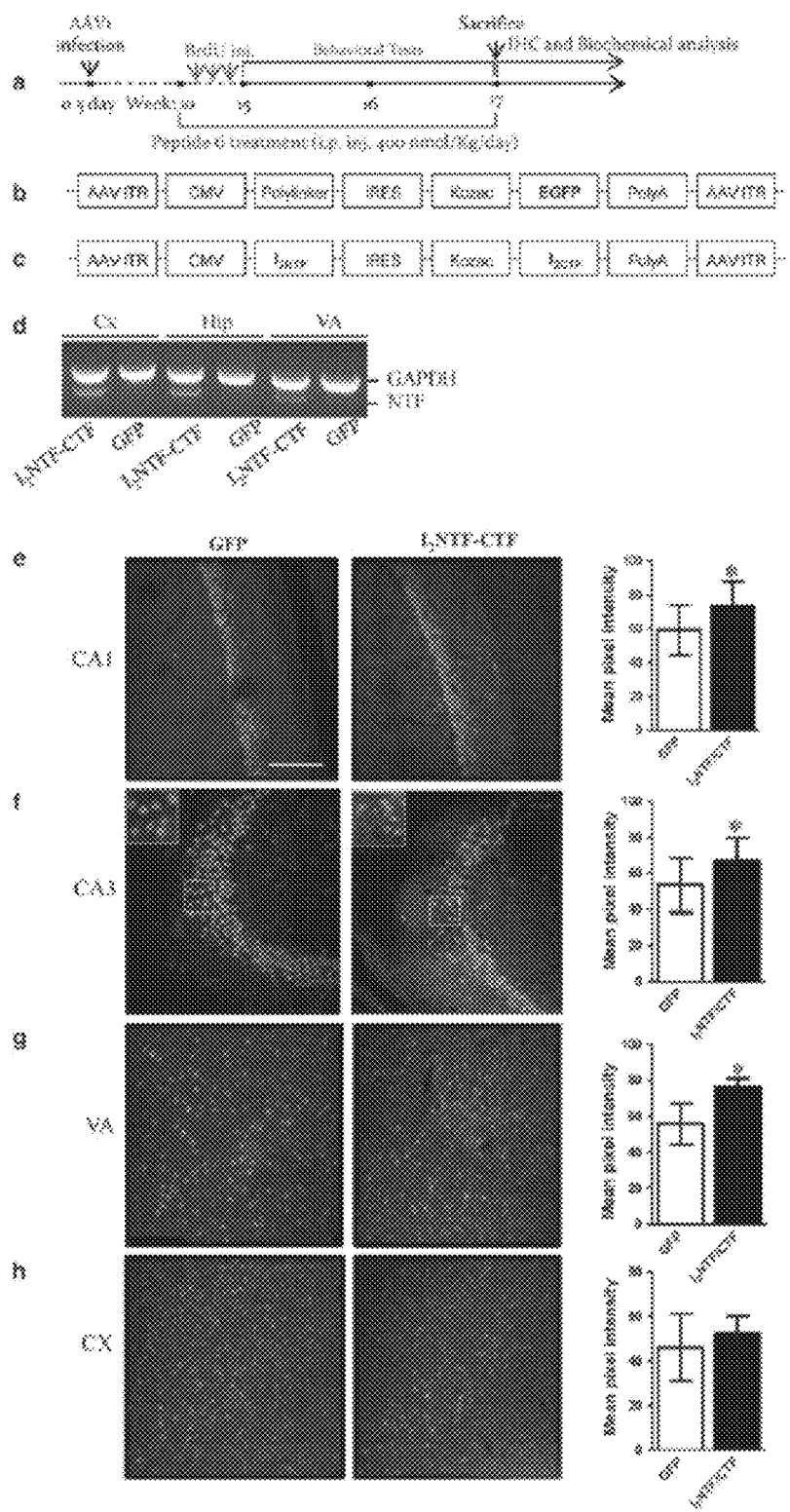
Figure 7:
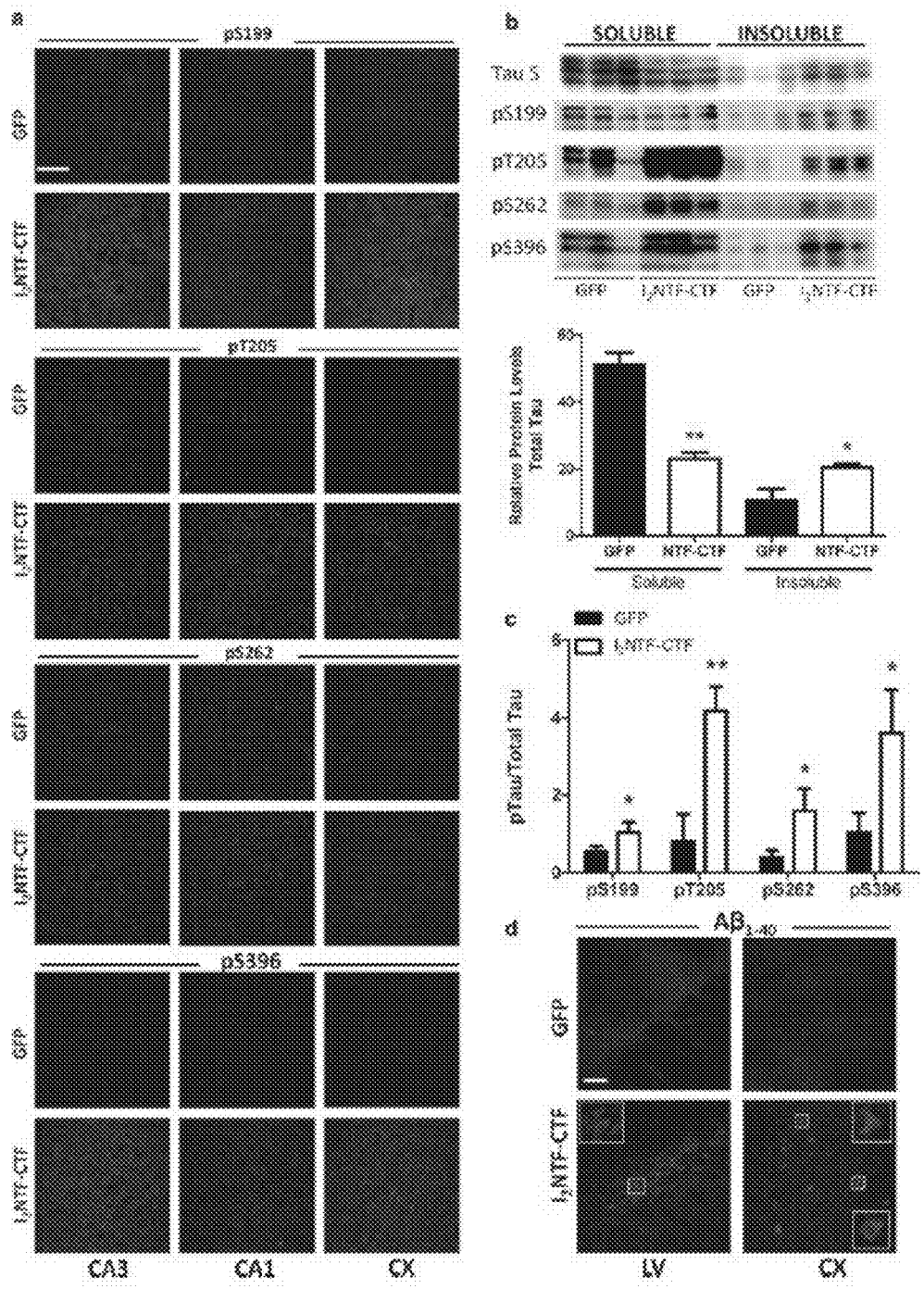

FIG. 6 is a series of graphs showing transduction of the brains of newborn rats with AAV1-$I_{2NTF-CTF}$ and stable expression of $I_{2NTF}$ and $I_{2CTF}$ 4 months postinjection, where (a) is a schematic representation of the outline of the study and includes linear maps of the AAV vector plasmids (based on pTRUF12). With the exception of the inverted terminal repeats (ITR) all viral genes had been removed and replaced with (b) GFP, or (c) $I_{2NTF}$ and $I_{2CTF}$. CMV cyglomegalovirus promoter, IRES internal ribosomal entry site from poliovirus. FIG. 6(d) shows that the mRNA expression of $I_{2NTF}$ was detected by reverse-transcriptase polymerase chain reaction (rt-PCR) of RNA extracted from cortex (CX), hippocampus (Hip) and ventricular area (VA) of GFP and $I_{2NTF-CTF}$ rats and separated by agarose gel. FIGS. 6(e)-(h) are representative confocal images illustrating the expression of $I_2^{PP2A}$ in GFP and $I_{2NTF-CTF}$ rats; the GFP auto fluorescence was negligible and the scale bar is 100 μm. Quantification of $I_2^{PP2A}$ staining fluorescence intensity in CA1 (e), CA3 (f) of the Hip, VA (g) and CX (h). Data are presented as mean±SD. *$p<0.05$ FIG. 7 is a series of graphs showing that $I_{2NTF-CTF}$ rats at 13 months of age show an increase in abnormal hyperphosphorylation and aggregation of tau and intraneuronal Aβ, where (a) is immunohistochemical staining with anti-tau pSer199, pThr205, pSer262, and pSer396 in CA3 and CA1 areas of the hippocampus and in the cerebral cortex (CX) in $I_{2NTF-CTF}$ and GFP control rats; (b) are Western blots and quantitation of sarkosyl-soluble and sarkosylinsoluble fractions from the cerebral cortices of $I_{2NTF-CTF}$ and GFP rats developed with a pan tau antibody Tau5 and phosphotau antibodies pSer199, pThr205, pSer262, and pSer396; (c) is abnormal hyperphosphorylation of tau (ptau/total tau) determined by quantitation of Western blots from the cerebral cortices of $I_{2NTF-CTF}$ and GFP rats; (d) is immunohistochemical staining with anti-Aβ40 (Invitrogen) of the lateral ventricle (LV) area and the cerebral cortex (CX) in $I_{2NTF-CTF}$ and GFP rats, where insets show intraneuronal Aβ, the magnification bar in a 50 μm, d 100 μm, and *$p<0.05$; **$p<0.01$.

Figure 8:
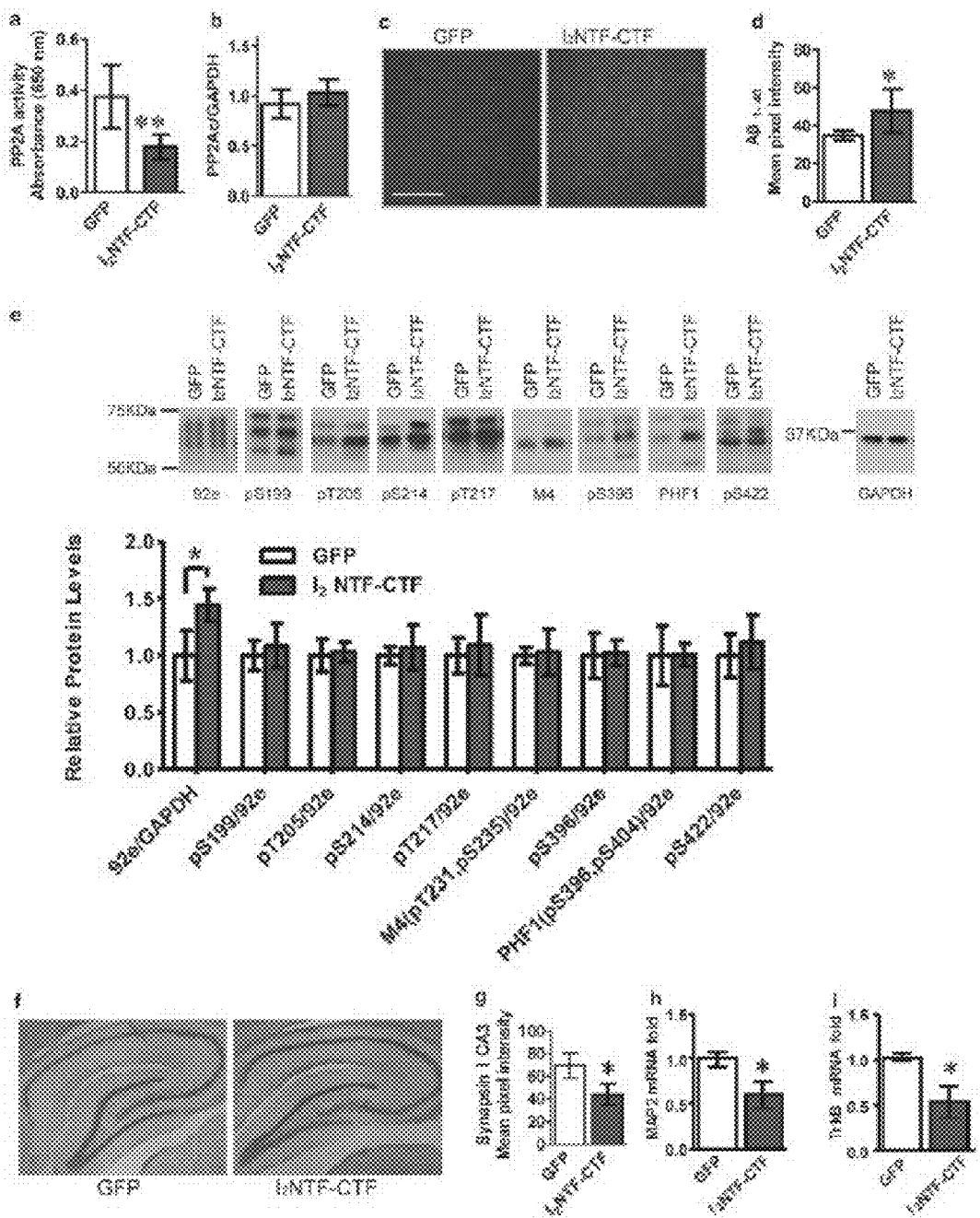

FIG. 8 is a series of graphs showing reduced PP2A activity, accumulation of Aβ1-40 and tau, and loss of neuronal plasticity in $I_{2NTF-CTF}$ rats, where (a) is PP2A activity in hippocampus extract of 4-month-old rats; (b) is PP2A catalytic subunit (PP2Ac) level assayed by Western blots in hippocampus homogenate; (c) is representative photomicrographs; and (d) is semi-quantitative expression level of Aβ1-40 in the cortex of GFP and $I_{2NTF-CTF}$ rats. FIG. 8(e) is representative Western blots developed with phospho-specific tau antibodies, where quantification of total tau, and hyperphosphorylation of tau at pSer199, pThr205, pSer214, pThr217, pThr231/pSer235, pSer396, pSer396/pSer404, and pSer422. Quantification of Western blots is shown as ±SD, normalized by GAPDH for total tau and for all the phosphorylation sites by total tau. FIG. 8(f) are images of Nissl staining of hippocampus from GFP and $I_{2NTF-CTF}$ rats; (g) is the expression level of synapsin I in CA3 of the hippocampus detected by immunohistochemistry1 (h) is mRNA expression level of MAP2, quantified by RTqPCR, in cortex form GFP and $I_{2NTF-CTF}$ rats; and (i) is mRNA expression level of TrkB receptor, quantified by RT-qPCR, in cortex form GFP and $I_{2NTF-CTF}$ rats, where *$p<0.05$.

Figure 9:
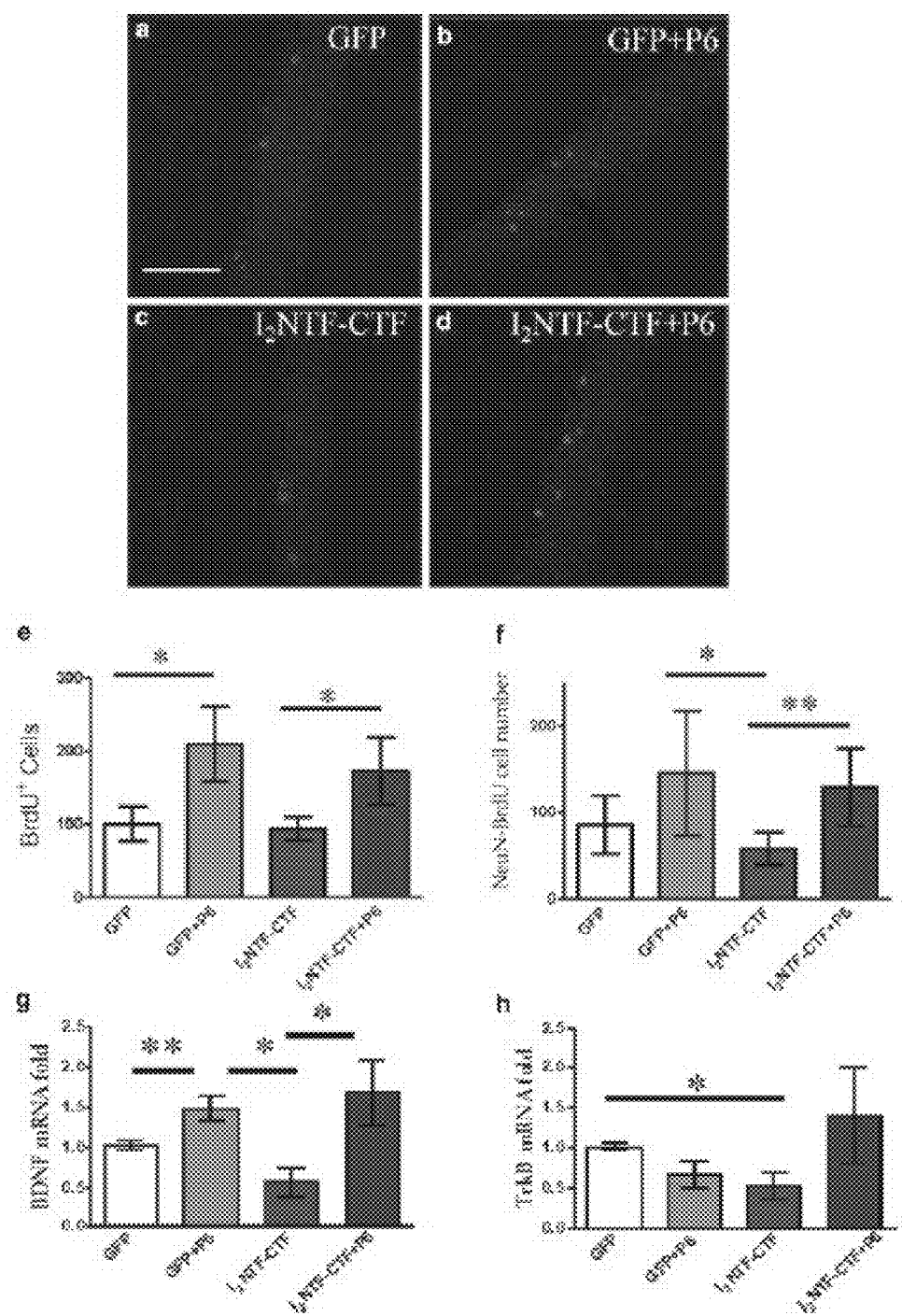

FIG. 9 is a series of graphs showing Peptide 6-induced increase in neurogenesis in $I_{2NTF-CTF}$ and GFP rats, where (a-d) are photomicrographs illustrating expression of BrdU-(red) and NeuN-positive cells (blue) and the scale bar 20 μm; (e) is the quantification of BrdUpositive cells in the iGCL of the DG; (f) is the co-localization of BrdUNeuN-IR cells in the SGZ; (g) is the mRNA expression level of BDNF and (h) is the TrkB receptor, quantified by RT-qPCR, in cortex from GFP and $I_{2NTF-CTF}$ rats treated with Peptide 6 (P6) or vehicle only, and data are expressed as the fold difference compared with vehicle-treated GFP animals (*$p<0.05$, **$p<0.01$).

Figure 10:
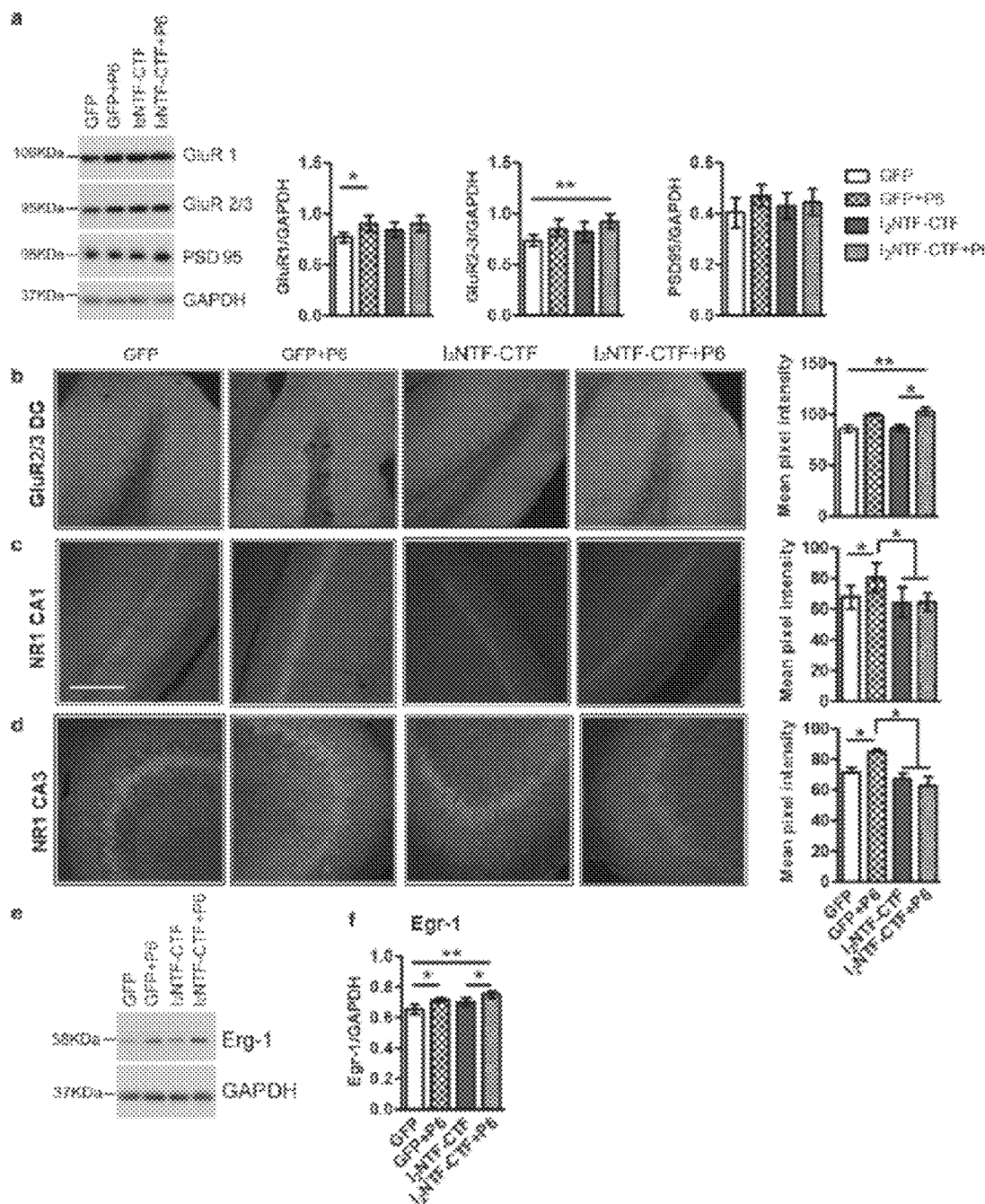

FIG. 10 is a series of graphs showing Peptide 6 (P6)-induced increase in glutamate receptor levels, where (a) is representative immunoblots and relative quantification in the whole hippocampus of GluR1, GluR2-3 and PSD-95; and representative photomicrographs and semi-quantitative expression level of GluR2/3 in DG (b), NR1 in CA1 (c), and CA3 (d) and the scale bar is 100 μm; (e) and (f) are representative Western blots and relative quantification of Egr-1 normalized against GAPDH in hippocampus homogenate, respectively, where *$p<0.05$, **$p<0.01$.

Figure 11:
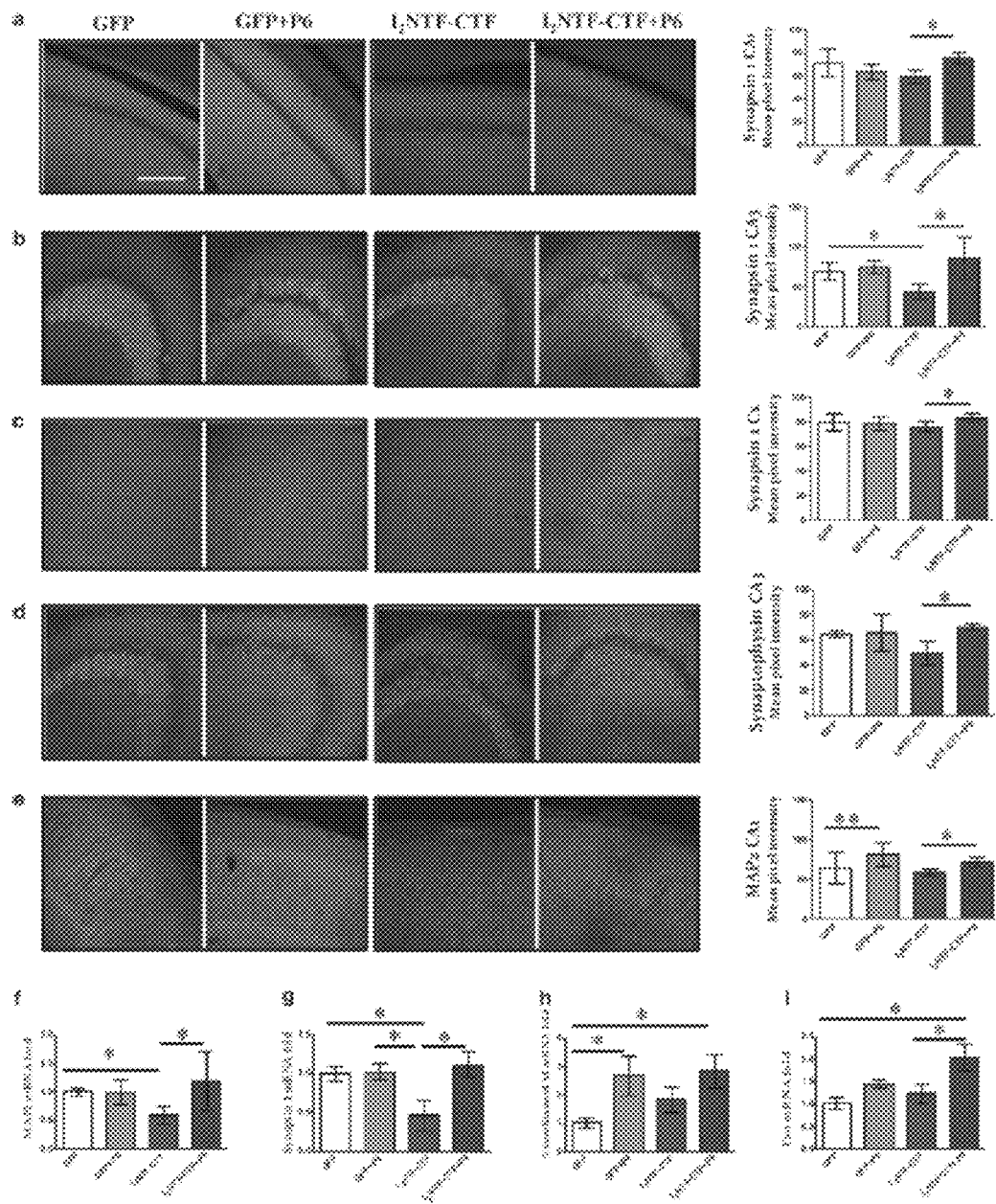

FIG. 11 is a series of graphs showing Peptide 6 (P6)-induced increase in dendritic and synaptic plasticity, where representative photomicrographs and semi-quantitative expression level of synapsin I in CA1 (a), CA3 (b) and cortex (c), synaptophysin in CA3 (d), and MAP2 in CA1 (e) and the scale bar 100 μm. The mRNA expression level of MAP2 are seen in (f), synapsin I (g), neurofilament M (h) and tau (i) quantified by RT-qPCR in cortex (*$p<0.05$, **$p<0.01$).

Figure 12:
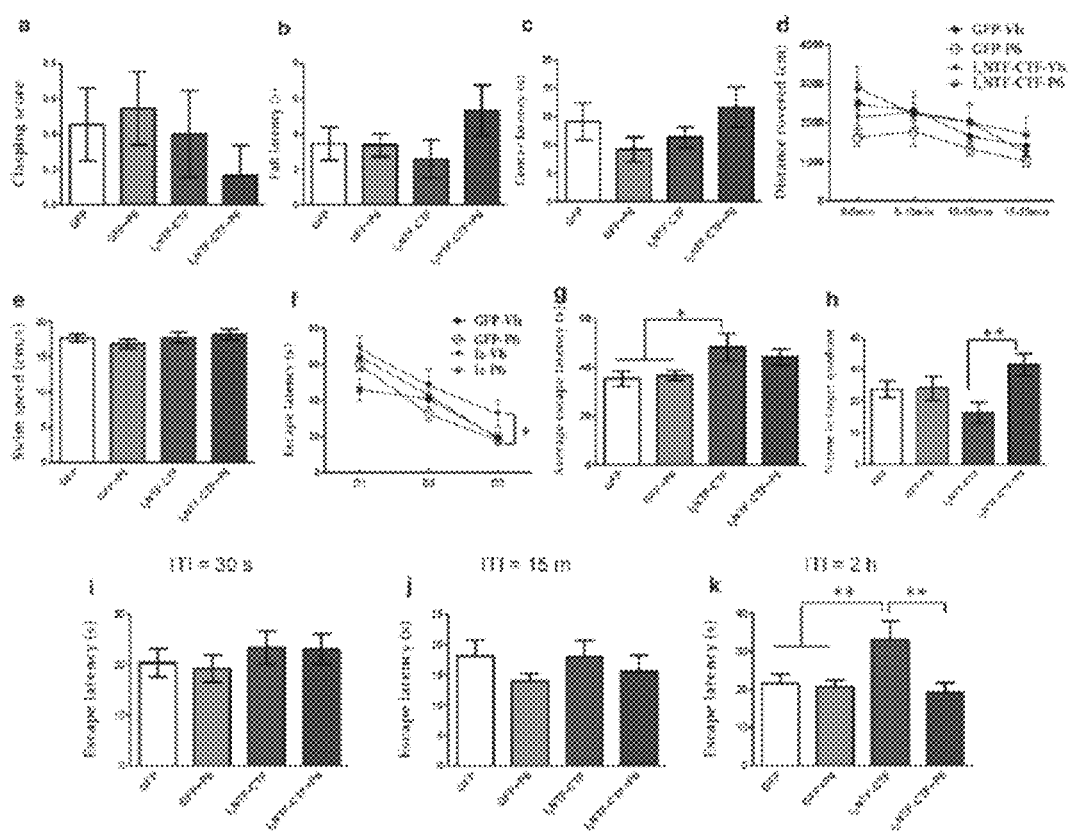

FIG. 12 is a series of graphs showing that treatment with Peptide 6 (P6) rescued cognitive impairments in $I_{2NTF-CTF}$ rats, where (a-d) show general behavior and. more particularly, (a) is clasping reflex, (b) is prehensile traction test, (c) is anxiety in the open field, (d) is exploration in the open field. FIG. 7(e)-(h) are spatial reference memory tasks, namely, (e) swim speed; (f) learning performance across training; (g) training performance, average escape latencies; (h) probe trial, % of time spent in the target quadrant. FIG. 7(i)-(h) are working memory tasks, namely, (i) Day 1 inter-trial intervals (ITI) 30 s; (j) Day 2 ITI 15 min; and (k) Day 3 ITI 2 h.

Figure 13:
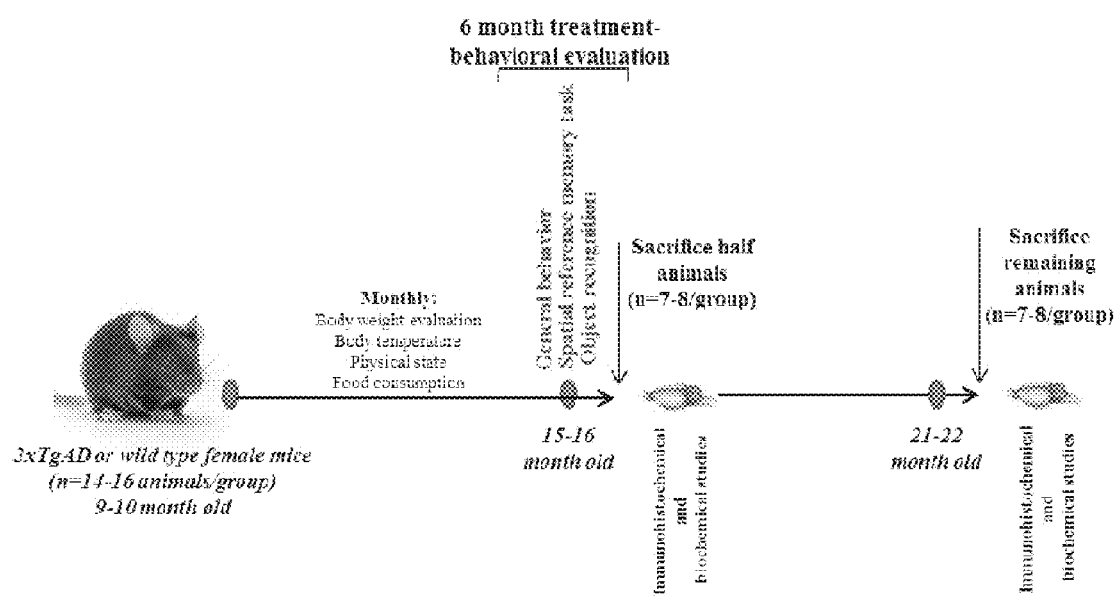

FIG. 13 is a schematic of the design of the study described in Example 2 below.

Figure 14:
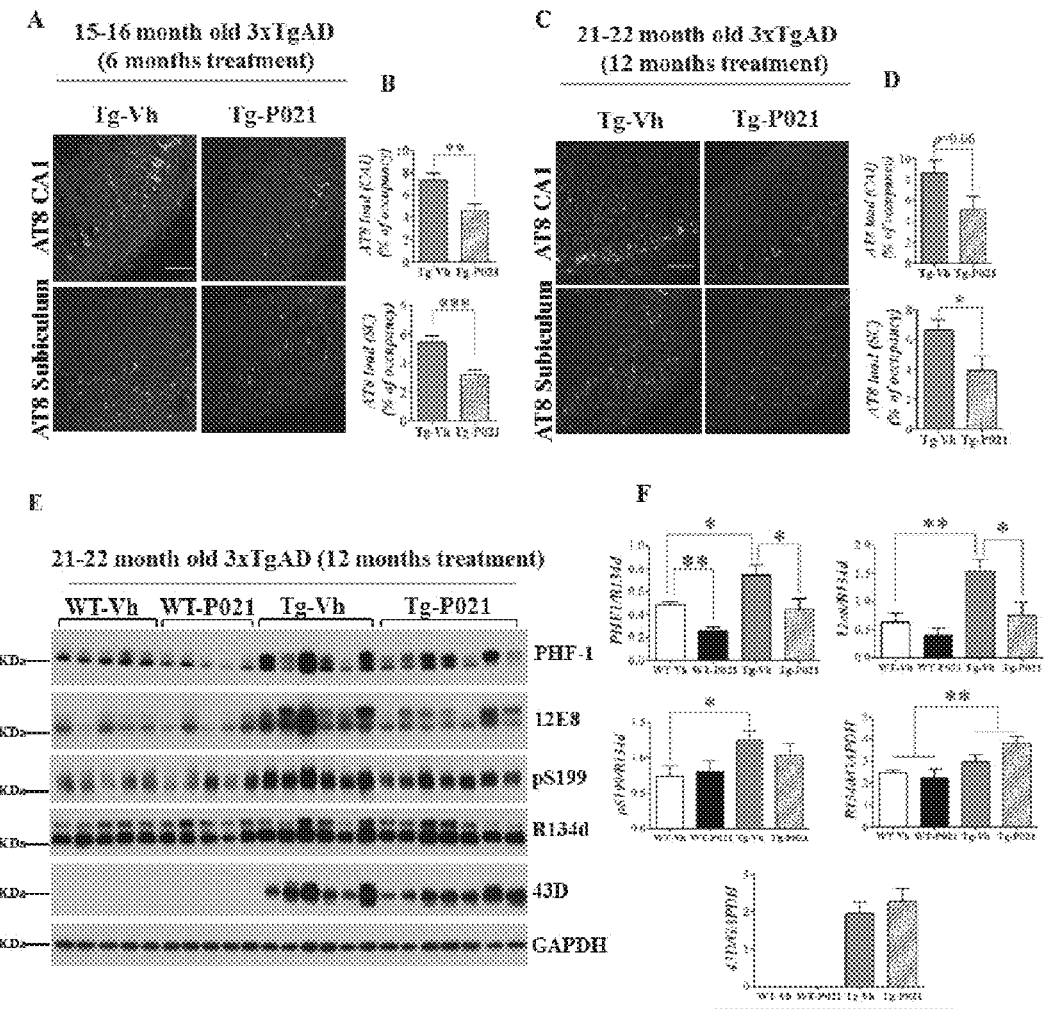

FIG. 14 is a series of graphs showing that chronic treatment with P021 reduced abnormal hyperphosphorylation of tau in 3×Tg-AD mice. (A-D) In the subiculum and the CA1 regions of the hippocampus, AT8 (tau pSer202, pThr 205) load was decreased by treatment with P021 in 3×Tg-AD mice (both 15-16 month old/6 months treatment group and 21-22 month old/12 months treatment group). (A) Representative photomicrographs illustrating AT8 immunoreactivity in the different regions of hippocampus from the 15-16 month old/6 months treatment group are shown. (B) The AT8 immunoreactive load was calculated as the percentage of area occupied by immunoreactive label. Quantification of the immunoreactivity is shown as mean±S.E.M. from Tg-Vh (n=7), and Tg-P021 (n=7). (C) Representative photomicrographs illustrating AT8 immunoreactivity in the different regions of hippocampus from the 21-22 month old/12 months treatment group are shown. (D) The AT8 immunoreactive load calculated as the percentage of area occupied by immunoreactive label is shown as mean±S.E.M. from Tg-Vh (n=6), and Tg-P021 (n=6). (E&F) Western blot analyses of tau pathology in 21-22 month old (12 months treatment) group. P021 treatment significantly reduced abnormal hyperphosphorylation of tau at sites pSerine 396/pSerine 404 (PHF-1) and pSerine-262/pSerine-368 (12E8). Pan-tau antibody, R134d did not show any significant difference between groups. Blots developed with human specific tau antibody 43D showed the protein expression only in 3×Tg-AD mice. Quantification of the Western blots is shown as mean±S.E.M. from WT-Vh (n=5), WT-P021 (n=5), Tg-Vh (n=6), and Tg-P021 (n=7). *p<0.05, p<0.01, and *p<0.001. Scale bar 100 µm.

Figure 15:
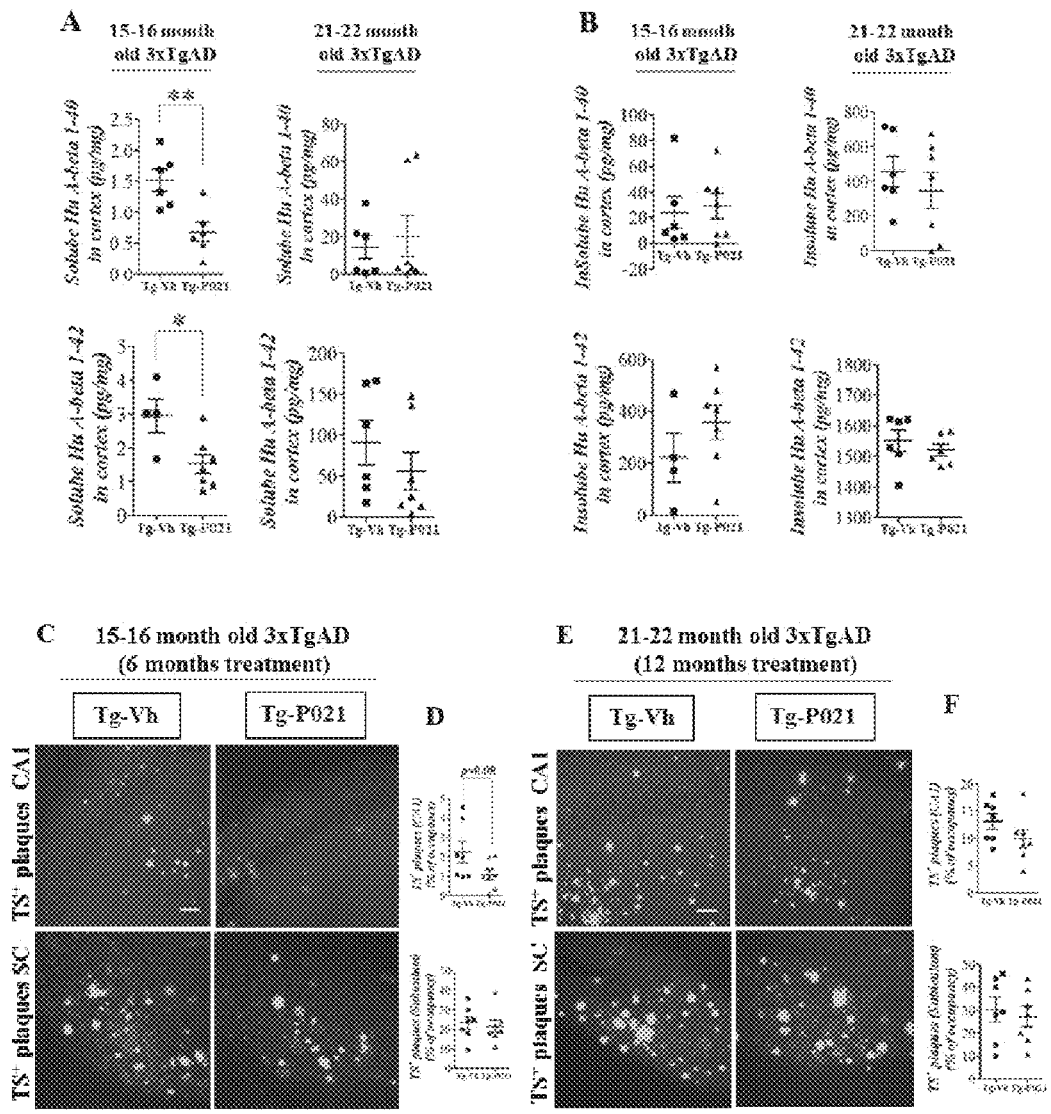

FIG. 15 is a series of graphs showing that chronic treatment with P021 reduced soluble Aβ in 3×Tg-AD mice. (A&B) ELISA quantification of soluble and insoluble Aβ 1-40 and Aβ 1-42 in the cortex revealed significant reduction of soluble Aβ in 15-16 month old group but not in 21-22 month old animals. No effect on insoluble Aβ was found. Quantification is shown as mean±S.E.M. from Tg-Vh (n=5-7) and Tg-P021 (n=6-7). (C&D) Representative photomicrographs illustrating TS$^+$ plaque load in the CA1 and subiculum regions of the hippocampus from 15-16 month old (6 months treatment) mice are shown. Quantification of TS$^+$ load is shown as mean±S.E.M. from Tg-Vh (n=7), and Tg-P021 (n=7). (E&F) Representative photomicrographs illustrating TS$^+$ plaque load in the CA1 and subiculum regions of the hippocampus from 21-22 month old (12 months treatment) mice are shown. Quantification of TS$^+$ load is shown as mean±S.E.M. from Tg-Vh (n=7), and Tg-P021 (n=6-7). Scale bar 100 µm.

Figure 16:
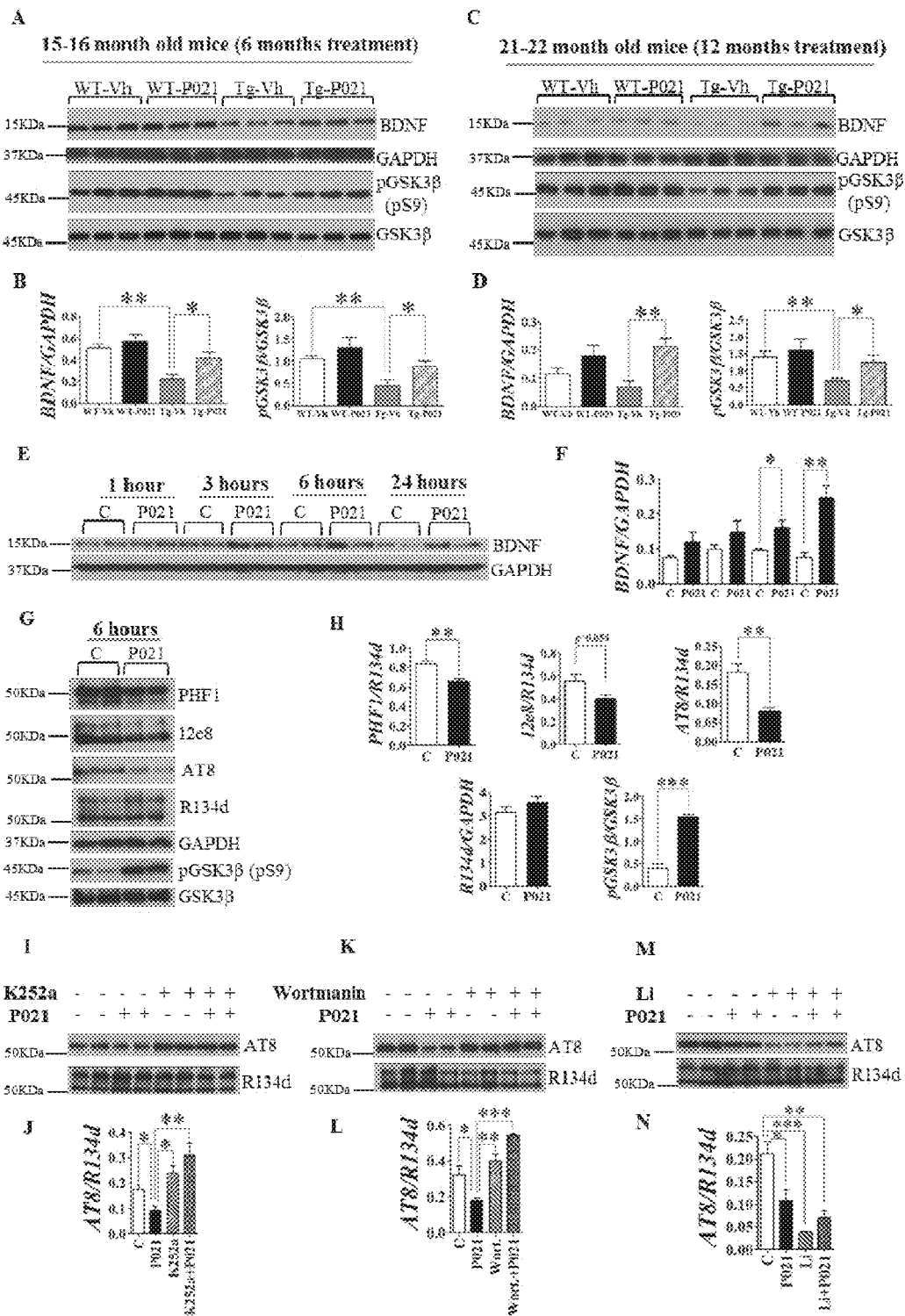

FIG. 16 is a series of graphs showing the disease modifying effect of P021 is mediated through BDNF/TrkB/PI3 kinase/AKT/GSK3β pathway. (A-D) Chronic treatment with Peptide 021 significantly increased BDNF expression and decreased GSK3β kinase activity in 3×Tg-AD mice. Western blot analysis of BDNF and Ser9 phosphorylated GSK3β normalized to total GSK3β expression in hippocampal homogenates from 15-16 month old/6 months treatment group [WT-Vh (n=5), Tg-Vh (n=5), and Tg-P021 (n=5)] and 21-22 month old/12 months treatment group [WT-Vh (n=6), Tg-Vh (n=6), and Tg-P021 (n=6)] are shown. (E&F) P021 increases BDNF expression in primary cortical neuronal cultures. (G&H) P021 treatment reduces abnormal hyperphosphorylation of tau and decreases GSK3β activity after 6 hours of treatment in primary cultured neurons. (I&J) Pre-treatment with Trk inhibitor, K252a, abolishes the effect of P021 on abnormal hyperphosphorylation of tau. (K&L) Pre-treatment with PI3-kinase inhibitor, wortmannin, reverses the effect of P021 on abnormal hyperphosphorylation of tau. (M&N) P021 could not significantly decrease the abnormal hyperphosphorylation of tau when GSK3β activity was inhibited by pre-treatment with lithium, a GSK3β inhibitor. For all primary neuronal culture experiments, quantification of data is based on two separate set of experiments. Quantification of all Western blots is shown as mean±S.E.M. *p<0.05, p<0.01, and *p<0.001.

Figure 17:
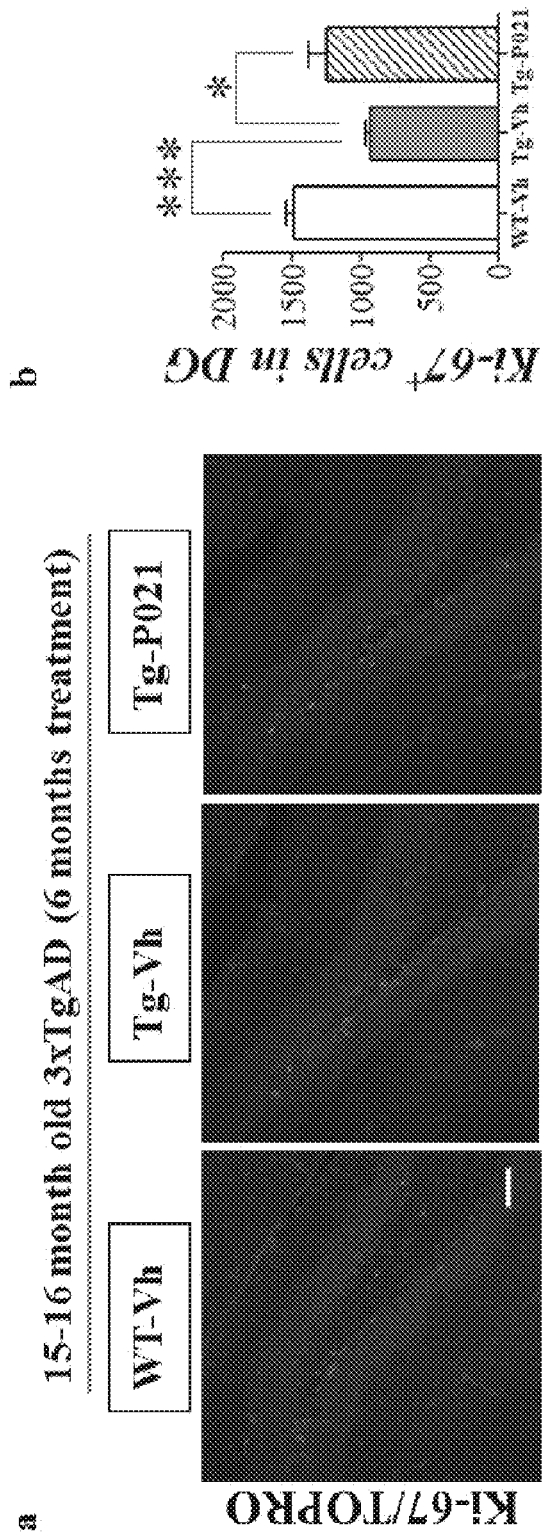

FIG. 17 is a series of graphs showing that chronic treatment with P021 rescued deficit in neurogenesis in 3×Tg-AD mice. (A&B) Representative photomicrographs illustrating Ki-67$^+$/TOPRO cells in the DG of hippocampus. Densitometric quantification of Ki-67$^+$ cells is shown as mean±S.E.M. from WT-Vh (n=6), Tg-Vh (n=7), and Tg-P021 (n=7). Scale bar 100 µm.

Figure 18:
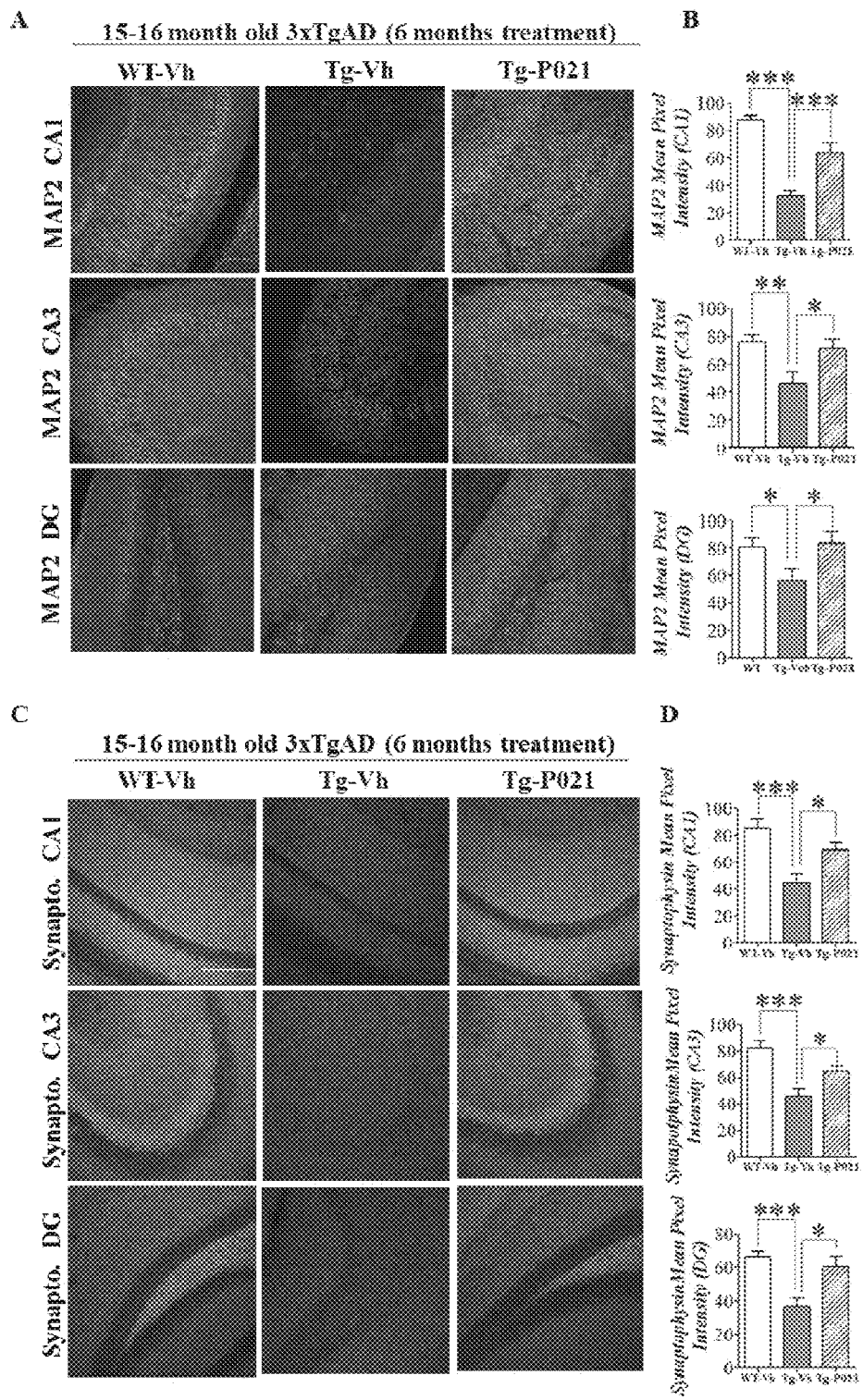

FIG. 18 is a series of graphs showing that chronic treatment with P021 rescued loss of dendritic and synaptic density in 3×Tg-AD mice. (A&B) The 15-16 month old 3×Tg-AD mice showed significantly reduced MAP2 fluorescence intensity in the CA1, CA3, and DG regions of the hippocampus which was significantly improved by oral treatment with P021. (A) Representative photomicrographs illustrating MAP2 immunoreactivity in the different hippocampal regions studied. (B) Densitometric quantification of the immunohistochemistry is shown as mean±S.E.M. from WT-Vh (n=6), Tg-Vh (n=7), and Tg-P021 (n=7). (C&D) 3×Tg-AD mice showed significantly reduced fluorescence intensity of the pre-synaptic marker, synaptophysin, in the CA1, CA3, and DG regions of the hippocampus. Treatment with P021 restored synaptophysin density to WT control levels. (C) Representative photomicrographs illustrating synaptophysin immunoreactivity in the different regions of hippocampus are shown. (D) Densitometric quantification of the immunohistochemistry is shown as mean±S.E.M. from WT-Vh (n=6), Tg-Vh (n=6), and Tg-P021 (n=6). *p<0.05, p<0.01, and *p<0.001. Scale bar 100 µm.

Figure 19:
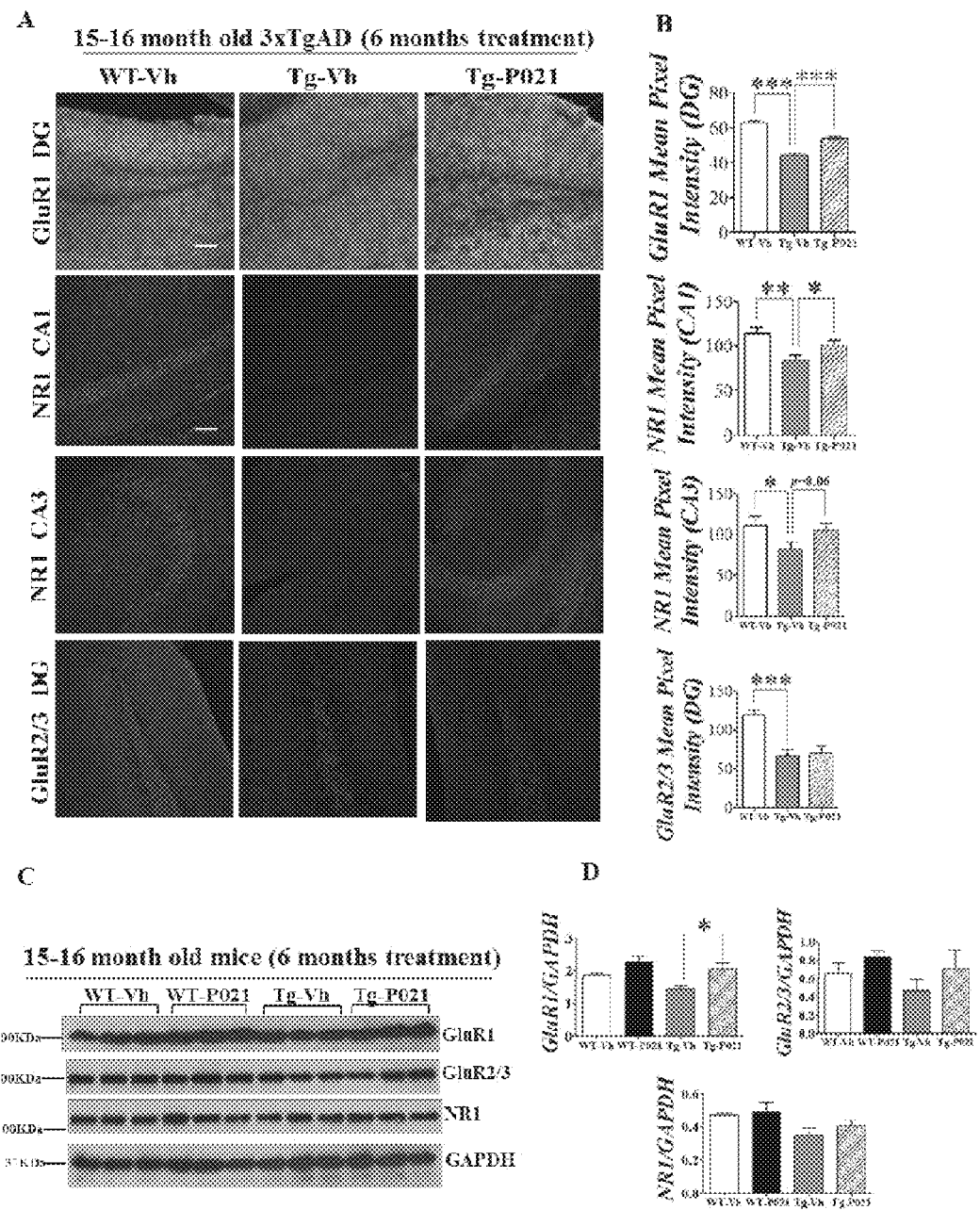

FIG. 19 is a series of graphs showing that chronic treatment with P021 increased expression levels of glutamate receptors in 3×Tg-AD mice. (A&B) The 15-16 month old 3×Tg-AD mice displayed significantly reduced density of AMPA receptor subunit GluR1 in DG region of the hippocampus, NMDA receptor subunit NR1 in CA1 and CA3 regions of the hippocampus, and AMPA receptor subunit GluR2/3 in DG region of the hippocampus. P021 treatment significantly improved the fluorescence intensity of GluR1 in DG and NR1 in CAL (A) Representative photomicrographs illustrating GluR1, NR1, and GluR2/3 immunoreactivity in the different regions of hippocampus are shown. (B) Densitometric quantification of the immunohistochemistry is shown as mean±S.E.M. from WT-Vh (n=6), Tg-Vh (n=6), and Tg-P021 (n=6). (C&D) Western blot analyses of glutamate receptors subunits expression in 15-16 month old (6 months treatment) group. Quantification of the Western blots is shown as mean±S.E.M. from WT-Vh (n=5), WT-P021 (n=5), Tg-Vh (n=6), and Tg-P021 (n=7). *p<0.05, p<0.01, and *p<0.001. Scale bar 100 µm.

Figure 20:
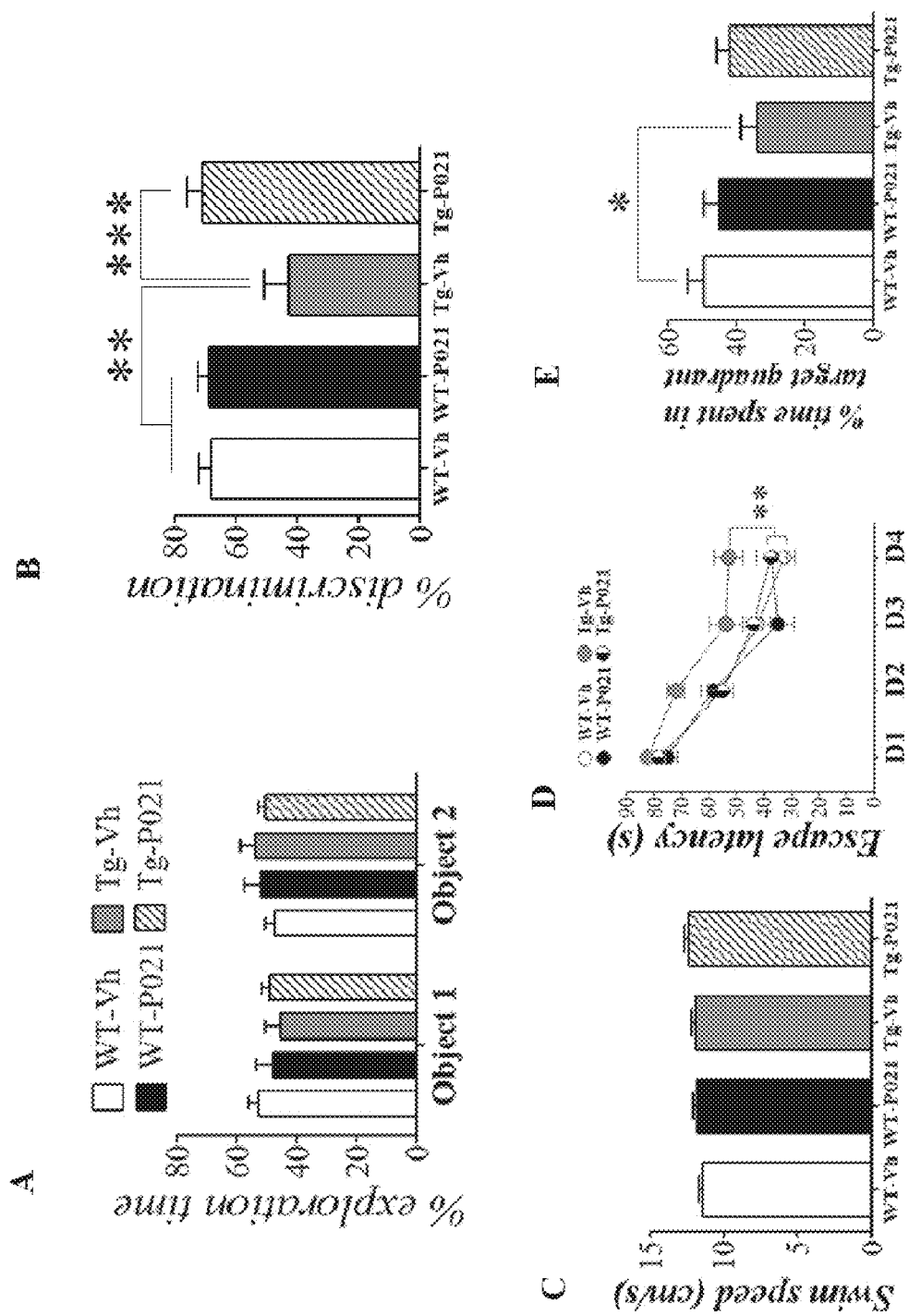

FIG. 20 is a series of graphs showing that chronic treatment with P021 rescued cognitive impairment in 15-16 month old 3×Tg-AD mice. (A&B) In the sample phase of the one-trial object recognition task (short-term memory), all animal groups similarly explored both objects whereas in the test phase of the one-trial object recognition task, 3×Tg-AD mice explored the familiar object more (discrimination index, 0.40), reflecting an impairment of discrimination. Treatment with Peptide 021 reversed this impairment. (C-E) In the spatial reference memory task in Morris water maze, 3×Tg-AD mice and WT controls displayed similar swim speed and treatment with P021 did not have any effect on velocity. During the training of the spatial reference memory task, performance of 3×Tg-AD mice was delayed compared to WT controls, but treatment with P021 reversed this impairment. In probe trial, 3×Tg-AD mice spent less time in the target quadrant. Data are shown as mean±S.E.M. Data based on WT-Vh (n=15), WT-P021 (n=14), Tg-Vh (n=15), and Tg-P021 (n=16). *p<0.05, p<0.01, and *p<0.001.

DETAILED DESCRIPTION OF THE INVENTION

The 3×Tg-AD mouse represents one of the most biologically relevant animal models described so far as it replicates all histopathological and behavioral hallmarks of AD. The 3×Tg-AD mice harbor three AD-related genetic loci: human PS1 M146V, human APPSWE KM670/671NL, and human tau P301L. These mice develop both amyloid plaques and neurofibrillary tangle-like pathologies in a progressive and age-dependent manner, starting at ~9 and ~12 months, respectively, but show cognitive impairment as early as ~5 months. Several other aspects of pathology also mimic AD pathophysiological changes and clinical phenotypes such as impairment of neurogenesis and synaptic plasticity, and cognitive decline, all of which precede Aβ and tau pathologies. For example, treatment of 6-7 month 3×Tg-AD mice for 6 weeks with Peptide 6 as explained in the parent application did not address tauopathies because, at this age, the animals do not develop tau pathology and hence are primarily a model of AD. At age 12 months onwards these animals do, however, develop tau pathology and thus also become an animal model of human tauopathies via the chromosome 17 (FTDP-17) tau mutation P301L when allowed to age to at least 12 months. As a result, the present application includes Examples using 9-10 month 3xTg-AD mice for 12 months treatment with Peptide 021 to establish that compounds according to the present invention will additional be effective in treating tauopathies.

EXAMPLE 1

In this Example, the chronic treatment with Peptide 21 is shown to restore neuronal and synaptic plasticity, associated cognitive impairments, and the underlying tau pathology in the later stage of the AD-like pathology. The 3xTgAD female mice and wild type (WT) controls were treated with Peptide 021 or vehicle diet (n=14-16/group) starting at 9-10 months of age. Treatment continued for a total period of 12 months. Animals were behaviorally tested after 6 months of treatment (15-16 months of age). After completion of the behavioral task, half of the animals (n=7-8/group) were perfused and brains were collected for immunohistochemical and biochemical analysis. Remaining animals were continued on Peptide 021/vehicle diet for another 6 months, and were sacrificed at 21-22 months of age for immunohistochemical and biochemical analysis (FIG. 1B).

Since administration of the full-length CNTF protein in human clinical trials is known to cause anorexia, skeletal muscle loss, hyperalgesia, severe cramps, and muscle pain, the general physical state of animals was carefully checked throughout the period of the study. During the entire 12 months of treatment, there were no observed alterations in general physical state, including grooming, posture, and clasping reflex, due to either the genotype or treatment with Peptide 021. The body temperature, body weight, and food consumption were evaluated monthly for the first 6 months of the study till the behavioral evaluation was performed. FIG. 2A represents body temperature follow up. Statistical analyses revealed a significant difference among groups (ANOVA, p=0.005). Post-hoc analysis showed a significant difference between WT animals treated with vehicle compared to other groups (Fischer's post-hoc test, p=0.022). As shown in FIG. 2B, statistical analysis on the body weight also showed significant difference among groups (ANOVA, p<0.001). Post-hoc analysis showed that WT animals treated with Peptide 021 were significantly heavier than the three other groups (Fisher's post-hoc test, p<0.025). WT mice, irrespective of the treatment, remained heavier than 3xTg-AD mice (Fisher's post-hoc test, p<0.05). The treatment with Peptide 21 did not induce any significant change of weight in 3xTgAD mice (Fisher's post-hoc test, p=0.233). FIG. 2C represents food consumption over the 6 months of treatment. Statistical analysis did not show any difference among groups (ANOVA, p=0.198).

FIG. 2D represents the animals' performance in the elevated plus-maze task. No effect of genotype or treatment was noted on the level of anxiety as the statistical analysis did not reveal any significant difference between groups in the amount of time spent in OA (ANOVA, p=0.7805). Previously, it was reported that 8-9 months old 3xTgAD mice displayed levels of anxiety which were marginally higher than the wild type controls. However, in the current study, the older 3xTgAD mice (15-16 months old) did not show such trends.

Locomotivity and motor coordination were evaluated in the accelerating Rotarod. 3xTgAD mice displayed higher scores than WT control mice (FIG. 2E; ANOVA; group effect: p<0.0001, Student's t-test, p<0.001). These results are surprising since it was shown that the P301L mutation affects the brain stem and consequently induces locomotor impairment. However, consistent with the present study, other studies have reported that at 5-7 months of age JNLP3 mice (harboring the P301L mutation) and βAPP+tau mice (harboring P301L mutation and hAPP Swedish K670N and M671L mutations) displayed higher scores than WT animals in both the Rotarod and the balance beam task. Also, in a previous study with 8-9 months old 3xTgAD mice, similar trends were found in the Rotarod performance. Except for this difference of performance due to the genotype, there was not observed any difference due to the treatment with Peptide 21 (WT-Vehicle versus WT-Peptide 21, Fischer's post-hoc test, p=0.7903; 3xTgAD-Vehicle versus 3xTgAD-Peptide 021, Fischer's post-hoc test, p=0.9231).

Exploratory activity was evaluated analyzing pattern and level of 15-minute free exploration of an animal in an arena. For rodents, the center of the arena is more anxiogenic than the periphery. Thus, measuring the time spent in the center of the arena, allows evaluating the potential effect of anxiety on exploratory behavior. As represented in FIG. 2F, the pattern of exploration of all groups was similar as all groups spent same time visiting the center of the arena (ANOVA, p>0.798). These data reaffirmed the similar anxiety levels detected among groups in the elevated plus-maze (see above).

To examine if animals displayed similar level of exploratory activity in a new environment, the total distance covered in the arena was analyzed in five intervals of 3 min each. All animals displayed similar level of exploration and covered comparable distance in the open field (FIG. 2G; ANOVA, p=0.712). These results suggested that neither the genotype nor the treatment with Peptide 21 altered general motivation for exploration of a new environment.

It is widely reported that in AD patients, during initial phases of the disease, the clinical symptoms include memory loss, particularly of recent events. In 3xTg-AD mice, the onset of cognitive impairment is known to occur around 5 months of age, in advance of overt plaque and tangle pathologies, and consists of hippocampus dependent impairment of spatial memory retention. To test whether treatment with Peptide 21 can alleviate early cognitive deficits in 3xTg-AD mice, a test for short-term memory and a hippocampal-dependent spatial reference memory was performed.

In the one-trial object recognition task, animals were exposed to two different objects which they have to identify as novel or familiar based on the memory of an earlier experience with one of the two objects they encountered in the same open-field. The familiar object is explored a shorter time than the novel object because the representation of the former is still available in memory. The one-trial object recognition task tests some aspects of episodic memory but is limited to memory of an object (what), the location of an object (where), and the context in which it was encountered (which). However, the temporal dimension of the episode remains inaccessible to the experimenter, and because of this reason this task in animals is considered a test of short term memory. The one-trial object recognition task is thought to critically depend on the entorhinal cortex, hippocampus and frontal cortex.

During the sample phase, all animals similarly explored both objects (FIG. 3A, ANOVA, p>0.999). During the test phase, 3xTg-AD mice displayed a significantly lower discrimination score than other groups (Student's t-test, p<0.003) (FIG. 3B). This result means that 3xTg-AD mice treated with vehicle did not preferentially explore the novel object. This null preference did not reflect a lack of interest for novelty but rather enhanced attraction for familiarity. This revealed that familiar-object representation was yet to be built and finalized, therefore requiring as much attention as the novel object to complete the encoding. In contrast, WT control mice and 3×Tg-AD mice treated with Peptide 021 displayed a clear preference for the novel object. This suggested that the representation of the familiar object started to be encoded, and then was less a subject of attention at the expense of the novel stimulus. These results showed that Peptide 021 can rescue short-term memory of 15-16 months old 3×Tg-AD mice.

The spatial reference memory task assesses hippocampus dependent reference memory in rodents, requiring that mice use a spatial navigational strategy to find a fixed submerged escape platform. The hippocampal system processes information about the relationships among distal environmental cues into a spatial map where spatial coordinates of the submerged platform are encoded. The hippocampus is also crucial for memory storage, consolidation, and restitution of the spatial information.

Because general behavioral evaluation demonstrated higher level of locomotivity for 3×TgAD mice compared to WT control animals (Rotarod test), the first parameter considered in the water-maze training was the swim speed of animals. It is indeed crucial to first elucidate if locomotivity was comparable between 3×TgAD and WT mice otherwise interpretation of data for learning and memory evaluation can be misinterpreted.

As shown in FIG. 3C, all animals displayed similar swim speed (ANOVA, $p<0.070$). The performance of the animals was analyzed as latency to reach the submerged platform. As depicted in FIG. 3D, there is a significant difference of learning among groups (ANOVA, $p=0.010$). Post-hoc analysis showed that 3×TgAD mice needed significantly longer latencies to reach the platform than WT control animals and 3×Tg-AD mice treated with Peptide 021 (Fisher's test, $p<0.006$). These results showed that treatment with Peptide 21 can alleviate impairment of spatial learning of 16 month-old 3×TgAD mice.

The probe trial allows evaluating the strength of the encoding of the spatial information. The more an animal searches for the platform in the target quadrant, the more the information of the spatial coordinates of the submerged platform was strongly encoded. As depicted in FIG. 3E, 3×Tg-AD mice treated with vehicle spent significantly less time in the target quadrant than WT mice treated with vehicle (Student's t-test, $p=0.032$). However, 3×Tg-AD treated with Peptide 21 displayed similar performance as WT controls. These results showed that at 15-16 months, the delay 3×TgAD mice displayed to learn spatial information is associated with a less robust encoding than controls after a similar training regimen, and that treatment with Peptide 21 can successfully rescue this impairment.

Synaptic loss, as reflected by changes in the presynaptic marker synaptophysin, correlates better with cognitive decline than either Aβ plaque load or neurofibrillary tangles in AD cases. 3×TgAD mice are known to develop deficits in synaptic plasticity by 6 months of age, including impairments in LTP and paired-pulse facilitation. Applicant had shown before that Peptide 6 can rescue deficits in neuronal plasticity in 3×TgAD mice. In the present example, chronic treatment with Peptide 021 was analyzed to determine whether it can reverse deficits in synaptic plasticity in these mice.

Synaptophysin is a glycoprotein of pre-synaptic vesicles involved in the vesicle trafficking machinery by regulating synaptic vesicle exocytosis. A significant decrease of synaptophysin immunoreactivity in 3×TgAD mice treated with vehicle compared to WT controls in the CA1 (ANOVA, $p<0.001$, Bonferroni's post-hoc test, $p<0.001$), in the CA3 (ANOVA, $p<0.001$, Bonferroni's post-hoc test, $p<0.001$), and in the dentate gyrus ((ANOVA, $p<0.001$, Bonferroni's post-hoc test, $p<0.001$) (FIG. 4A) was observed. Peptide 21 treatment was able to rescue the deficit in these hippocampal regions in the 3×TgAD mice (Bonferroni's post-hoc test, $p<0.001$, $p<0.01$, and $p<0.05$ for CA1, CA3, and DG regions respectively) (FIG. 4A).

Synaptic pruning is a feature of AD pathology. The expression of AMPA receptor subunits was evaluated due to their essential role for synaptic transmission and LTP as well as cellular mechanisms which are connected with learning and memory. Peptide 21 was able to induce a significant increase of the GluR1 subunit of AMPA receptors in the dentate gyrus region of the hippocampi of 3×TgAD mice which showed deficit as compared to WT. (WT-Vh versus Tg-Vh, Student's t-test, $p=0.035$; Tg-Vh versus Tg-P021, Student's t-test, $p=0.048$) (FIG. 4B).

Biochemical analysis was used pre- and post synaptic structures to further evaluate the effect of Peptide 021 on synaptic plasticity (FIG. 4C). Western blots developed with anti-synapsin I showed a marginally significant increase in WT animals (WT-Vh versus WT-P021, Student's t-test, $p=0.054$), however, the difference between Tg-Vh and Tg-P021 did not reach statistical significance (Student's t-test, $p=0.1419$). Similar trends were observed with the post-synaptic marker, PSD95 (WT-Vh versus WT-P021, Student's t-test, $p=0.012$; Tg-Vh versus Tg-P021, Student's t-test, $p=1.000$).

Altogether these results suggest that chronic treatment with Peptide 21 can rescue deficits in expression of synaptic plasticity markers in 3×TgAD mice. The increase in synaptic plasticity can be the underlying mechanism by which the peptide ameliorated the cognitive deficits in these mice.

In AD patients, Aβ and tau pathologies are associated with unsuccessful neurogenesis and loss of neuronal plasticity. It was observed that shifting the balance from neurodegeneration to regeneration of the brain by CNTF derived Peptide 21 rescued deficits in synaptic plasticity and cognition. So, the next important step was to evaluate the effect of the peptide on these pathologies. In 3×Tg AD mice, the tau pathology occurs at late age and is first visible in the CA1 pyramidal neurons, becoming readily apparent in the hippocampus and in cortical structures by 12-15 months of age. To finally investigate whether Peptide 21 had any effect on the development of tau pathology, immunohistochemical studies were conducted in 15-16 months old (6 months treatment) animals (FIG. 5A) and biochemical studies in 21-22 months old animals (12 months treatment) (FIG. 5B).

Immunohistochemistry with AT8 (anti-pSer202/pThr205 tau) antibody revealed specific immunoreactivity in the subiculum and in the CA1 region of the hippocampus of 15-16 months old (6 months treatment) animals (FIG. 5A). A significant reduction in Peptide 021 treated 3×TgAD animals was seen as compared to the vehicle treated group (Subiculum, Student's t-test, $p=0.0014$ and CA1, Student's t-test, $p<0.0001$). Hyperphosphorylated microtubule-associated protein tau is the major component of the paired helical filament of Alzheimer's disease, and its reduction by chronic treatment with Peptide 21 shows that peptide has a neurprotective effect against tauopathy in the animal model of the disease.

As expected, the Western blots from hippocampi of 21-22 months old animals (12 months treatment) developed with the human specific tau antibody 43D showed human tau expression only in 3×Tg-AD, but not the control mice; no significant effect of the peptide was noted. The Western blots developed with phosphorylation independent tau antibody, R134d did not reveal any significant difference between groups; however, there was a trend towards increased expression in 3×TgAD mice. Western blots with 77G7 antibody (reactive to all six isoforms of tau) did not show any significant difference between groups (ANOVA, p=0.113). The Western blots developed with pan-tau antibody, 92e, also did not show any significant difference between groups (ANOVA, p=0.0755).

A significant increase in PHF-1 (pSerine 396/pSerine 404) was observed in vehicle treated 3×TgAD mice as compared to WT (Student's t-test, p=0.0345). Chronic treatment with Peptide 21 significantly reduced the abnormal hyperphosphorylation at this site (Student's t-test, p=0.0382). Similarly, Western blots developed against pSerine-262/pSerine-368 antibody, 12E8, showed significant increase in vehicle treated 3×TgAD mice compared to WT controls (Student's t-test, p=0.0084). Peptide 21 treatment significantly reduced the expression in 3×TgAD mice (Student's t-test, p=0.0306).

A significant increase in the abnormal hyperphosphorylation of tau pSerine 199 (Student's t-test, p=0.024) but no effect of Peptide 21 was observed (Student's t-test, p=0.3170). A significant increase in AT8 (pSerine 202/pThreonine 205) was observed in vehicle treated 3×TgAD mice as compared to WT (Student's t-test, p=0.0078). Chronic treatment with Peptide 21 did not affect the abnormal hyperphosphorylation at this site (Student's t-test, p=0.948). This was different from the significant reduction noted in the expression of AT8 in 3×TgAD mice treated with Peptide 21 by using immunohistochemical quantification in 6 month treated animals. However, this could be explained partially by the fact that AT8 expression was noted only in the CA1 and subiculum regions of the hippocampus, and immunohistochemistry is known to be more precise for detecting region specific changes than Western blotting.

Taken together, these results show that chronic treatment with Peptide 21 significantly reduced abnormal hyperphosphorylation of tau both in 15-16 months and 21-22 months old animals.

FIG. 1A shows the structure and design of the peptidergic compound used in the study. Peptide 21 (Ac-DGGL$^4$G-NH$_2$) which corresponds to amino acid residues 148-151 of human CNTF (FIG. 1A) was identified as an active region of this neurotrophic factor by epitope mapping of neutralizing antibodies to CNTF. The peptide was synthesized and purified by reverse phase HPLC to >96% purity, as described previously.

The 3×Tg-AD homozygous mice harboring PS1M146V, APPSwe, and tauP301L transgenes were obtained from Frank LaFerla through Jackson Laboratory (New Harbor, Me., USA). The background of the 3×Tg-AD mice is a hybrid 129/Sv 9 C57BL/6. NonTg wild type (WT) mice used were from the same strain and genetic background and were obtained from Jackson Laboratory. Mice were housed and bred in accordance with approved protocols from our Institutional Animal Care and Use Committee, according to the PHS Policy on Human Care and Use of Laboratory animals (revised March, 2011). This study was performed on homozygous 3×Tg-AD female mice. Mice were group-housed (4 animals per cage) with a 12:12 h light/dark cycle and with ad libitum access to food and water.

3×Tg-AD mice (9-10 months old) (n=15-16) and WT controls (n=15-16) were treated orally with Peptide 021 or vehicle diet for 12 months. Treatment was administered as 60 nmolpeptide/g formulated diet (Research Diets; New Brunswick, N.J.). The vehicle-treated control animals received the same diet but without the peptide. Animals were behaviorally tested after 6 months of treatment (15-16 months of age). First general behavioral battery of tests was done, and then cognitive tests were carried out. After completion of the behavioral task, half of the animals (n=7-8/group) were perfused and brain tissue was collected for immunohistochemical and biochemical analysis. Remaining animals were continued on Peptide 021/vehicle diet for another 6 months, and were sacrificed at 21-22 months of age for immunohistochemical and biochemical analysis (FIG. 1B).

The physical state and condition of the animals were carefully checked throughout the treatment by evaluating grooming, posture, physical state, and clasping reflex. Bodyweight, body temperature, and food consumption during the first 6 months were also recorded.

As a test which has traditionally been used to evaluate anxiety/emotionality, the elevated plus-maze consisted of four arms (30×5 cm) connected by a common 5×5 cm center area. All arms and the central area were constructed with dark opaque Plexiglas. Two opposite facing arms were open (OA), whereas the other two facing arms were enclosed by walls (CA, 20 cm height). The entire plus-maze was elevated on a pedestal to a height of 82 cm above floor level. Ambient luminosity was maintained at 60 Lux to control the anxiogenic feature of light for rodents. During a single 8-min session, an animal was placed onto the central area. A videotracking system detected the presence of the animal and the time it spent in the different zones of maze-arms. Between each session, any feces were cleared from the maze, and the maze floor was cleaned with 70% alcohol to remove any urine or scent cues. For each animal, the number of CA entries, OA entries, and amount of time spent in CA and OA were recorded. As OA are more anxiogenic for rodents than CA, the percentage of time spent in OA was calculated to evaluate anxiety-like behavior of animals. The percentage of time spent in OA corresponds to the ratio of the time spent in OA compared to the time spent in all arms (OA+CA).

Testing on accelerating Rotarod was conducted by giving each mouse two sessions of three trials each with the motor in accelerating mode (factory settings). In this mode, the rotating speed increased steadily, at a rate of 0.02 cm/s, from 4 to 40 rpm. The latency to fall off the Rotarod was calculated. Inter-trial intervals were 10-15 min for each mouse.

Exploratory activity was evaluated analyzing pattern and level of 15-minute free exploration of an animal in an arena. The testing apparatus was a classic open field (i.e. a PVC square arena (50×50 cm), with walls 40 cm high). The open field was placed in a part of the room separated from the experimentor with a black opaque curtain. The open field was surmounted by a video camera connected to a computer tracking animals. Data collection was performed using a video tracking system (Smart version 2.0.14 software, Pan Lab/San Diego Instruments). The data was analyzed time spent in the center of the arena (measure of anxiety) and distance covered (measure of exploratory activity) during the single 15-minute testing session.

The test used was an adaptation of the procedure previously described by Sargolini and collaborators. The testing apparatus was a classic open field (i.e. a PVC square arena, 50×50 cm, with walls 40 cm high). The open field was placed in a part of the room separated from the investigator with a black opaque curtain. The open field was surmounted by a video camera connected to a computer. Three objects were employed in this task. The general procedure consisted of three different phases: a familiarization phase (4 sessions of 10 min each on 4 consecutive days), a sample phase (5$^{th}$ day), and a test phase (5$^{th}$ day). On the first four days, mice were individually submitted to the familiarization session during which they were introduced in the empty arena in order to become familiar with the apparatus. On the fifth day, each mouse was first submitted to the sample phase (session 1, ten minutes) for which two identical objects were placed in a symmetric position from the centre of the arena. After a 15 minute delay during which the mouse returned to its home cage, it was reintroduced in the arena to perform the test phase (session 2, 10 min). The mouse was then exposed to two objects: a familiar object (previously presented during the sample phase) and a new object, placed at the same location as during the sample phase. Data collection was performed using a video tracking system (Smart version 2.0.14 software, Pan Lab/San Diego Instruments). Object discrimination was calculated as follows:

OD=(time spent close to new object)/(time spent close to new object+time spent close to old object)×100

The test used was an adaptation of the procedure previously described by Morris et al (20). The procedure was performed in a 180-cm diameter circular tank. The pool was filled with water (21±1° C.) made opaque by adding white non-toxic paint. Acquisition started with the escape platform (13 cm diameter submerged 1 cm below water surface) in the Northwest quadrant, and each animal was given 90 s to find the platform. If the mouse did not find the platform in 90 s, it was gently guided to it. At the end of each trial, the mouse was left on the platform for 20 s, then dried, and returned to its home cage until the next trial. Three such acquisition trials were given on each day for four consecutive days. Each animal performed a total of 12 trials corresponding to a partial training of the spatial reference memory task. The measures of learning were the time and distance covered to reach the escape platform. For the probe trial, the tank was divided into four imaginary quadrants and a small zone where the escape platform had been. The measures of retention were the percent of time spent and the percent of distance covered in each quadrant. Swim speed was also calculated. Mice behavior in the water-maze was monitored by a Samsung Digital Camera (SDC 4304) mounted to the ceiling and tracked and timed using a SMART (PanLab/San Diego Instruments) version 2.0.14 software.

After completion of the behavioral task at six months treatment (15-16 months old animals), half of the animals (n=7-8/group) were perfused and brain tissue was collected for immunohistochemical and biochemical analysis. Remaining animals were continued on Peptide 021/vehicle diet for another 6 months, and were sacrificed at 21-22 months of age for immunohistochemical and biochemical analysis.

Animals were anesthetized with an overdose of sodium pentobarbital (125 mg/kg) and transcardially perfused with 0.1 M phosphate buffered saline (PBS). After perfusion, the brains were removed from the skull; the left hemisphere was dissected into hippocampus and cortex and then immediately frozen in dry ice for biochemical analysis, and the right hemisphere was fixed in 4% paraformaldehyde in 0.1 M PBS for at least 24 h at room temperature. Tissues were then post-fixed in a 30% sucrose solution at 4° C. overnight. 40-µm sagittal sections of the entire hippocampus were cut on a freezing microtome. The sections were stored in glycol anti-freeze solution (Ethylene glycol, glycerol and 0.1 M PBS in 3:3:4 ratio) at −20° C. until further processing.

Immunohistochemistry was performed on free-floating sections and every tenth brain section was chosen for densitometry and quantification. For immunohistochemistical quantification, brain sections of 5-6 animals per group were randomly selected and analyzed. The primary antibodies against the following proteins were used at the indicated dilution: rabbit polyclonal anti-synapsin I (1:2,000; Stressgen, Victoria, BC, Canada), mouse monoclonal anti-synaptophysin (1:200; Millipore, Temecula, Calif., USA), rabbit polyclonal anti-GluR1 (1:300; Millipore, Temecula, Calif., USA), and anti-pSer202/pThr205, AT8 (1:500; ThermoScientific, Rockford, Ill., USA). The following secondary antibodies were used: Alexa 488-conjugated goat antimouse IgG antibody (1:500, Molecular Probes, Carlsbad, Calif., USA) and Alexa 594-conjugated goat anti-rabbit IgG antibody (1:500, Molecular Probes, Carlsbad, Calif., USA).

For densitometry, the region of interest was outlined on every tenth section. For synaptophysin, the entire area of the GCL, the CA1, and the CA3 of the hippocampus and parietal association and frontal cortices were analyzed. For immunohistochemistry with antibody to tau, only brain regions showing positive specific staining were quantified, namely the CA1 of the hippocampus and the subiculum. Maximum projection images were then generated based on confocal z-stacks using Nikon 90i fluorescent microscope equipped with Nikon C1 three-laser confocal system and a Nikon DS U1 digital camera. The antibody staining was quantified by measuring mean pixel intensity (MPI) with the software Image-ProPlus 5.0 (Media Cybernetics, Silver Spring, Md., USA).

Brain tissue stored at −80° C. from each PBS perfused mouse was homogenized in a Teflon-glass homogenizer to generate 10% (w/v) homogenate. The homogenization buffer contained 50 mM Tris-HCl, pH 7.4, 0.25 M sucrose, 2 mM EDTA, 10 mM b-mercaptoethanol plus the following protease and phosphatase inhibitors: 0.5 mM AEBSF, 8 lg/ml aprotinin, 10 lg/ml leupeptin, 4 lg/ml pepstatin, 5 mM benzamidine, 20 mM b-glycerophosphate, 50 mM sodium fluoride, and 1 mM sodium vanadate. Protein concentration of each brain homogenate was determined by modified Lowry assay. The tissue homogenates were boiled in Laemmli's buffer for 5 min, and then subjected to 10% SDS-polyacrylamide gel electrophoresis, followed by transfer of separated proteins on 0.45 µm immobilon for Western blots. The Western blots were developed with antibodies to synaptic markers, tau, phosphor-tau. For loading control, the blots were developed with mAb to GAPDH (1 lg/ml; Abcam, Cambridge, Mass., USA). Immunoreactive protein bands were visualized with enhanced chemiluminescence (ECL) reagents (Pierce, Rockford, Ill., USA). The ECL films of the blots were scanned and analyzed using Multi Gauge software version 3.0 (Fujifilm, Tokyo, Japan). Mean values for each group of animals were analyzed by t test. Differences with $p<0.05$ were considered significant.

The statistical analyses were conducted using SPSS version 17.0 (© SPSS Inc., 1989-2007, Chicago, Ill., USA), StatView, SASv5 software (SAS Institute, Cary, N.C., USA), and GraphPad Prism version 5.0 (GraphPad software inc., La Jolla, Calif., USA). Data are presented as mean±S.E.M. For analysis involving multiple groups, one-way ANOVA with post hoc Fisher's/Tukey's/Newman-Keul's/Bonferroni's test (as indicated) was used. For all other comparisons (including inter-group comparisons), Student's t-test was used. For all purposes, $p<0.05$ was considered as statistically significant.

EXAMPLE 2

In another study, a blood-brain barrier (BBB) permeable CNTF derived peptidergic compound, Peptide 021 (P021) (SEQ. ID. NO. 3) was used, which exerts neurogenic and neurotrophic effects mainly by inhibiting leukemia inhibitory factor (LIF) signaling pathway and enhancing brain derived neurotrophic factor (BDNF) expression by increasing its transcription. Chronic treatment with P021, administered in diet to triple transgenic AD (3×Tg-AD) mice, can not only restore impairments in neurogenesis, dendritic and neuronal plasticity, and cognition at moderate stage of the disease but also strongly attenuate tau pathology both at moderate and severe stages of the disease. P021 also exerted a marginal reduction in Aβ pathology at moderate stage of the disease. This disease modifying effect of P021 was probably due to the increased BDNF expression-mediated reduction in glycogen synthase kinase-3β (GSK3β) activity we found in the P021-treated 3×Tg-AD mice, and further confirmed in P021-treated primary cultured cortical neurons.

FIG. 1 shows the structure of the peptidergic compound P021 (Ac-DGGL$^4$G-NH2) (SEQ. ID. NO. 3) which corresponds to a biologically active region of human CNTF (amino acid residues 148-151) to which adamantylated glycine was added to increase its stability and lipophilicity. The peptide was synthesized and purified by reverse phase HPLC to >96% purity, as described previously. The sequence of the peptide was confirmed by mass spectrometry.

The studies on the plasma stability and stability in gastric and intestinal juices of P021 were performed by EVER NeuroPharma GmbH, Unterach, Austria. The plasma stability was analyzed in human pooled plasma in PBS (1:1) using different concentrations of P021 (1 μM, 1 mM, and 40 mM). The acetonitrile with internal standard albendazole was used as stop solution, and peptide concentrations were measured by HPLC. The plasma concentration of P021 reached 50% of the initial amount in 180-200 minutes (corresponding to a half life of >3 hours). For 1 L artificial gastric juice, 2 g of NaCl and 3.2 g of pepsin were dissolved in 100 mL water; 80 mL of 1M HCl was then added, pH was adjusted to 2.5+0.5 and the final volume was made up to 1 L with water. The P021 was stable (>90%) in artificial gastric juice as analyzed up to 30 minutes. For 1 L artificial intestinal juice, 6.8 g sodium dihydrophosphate and 10 g Pancreatin were dissolved in 380 mL 0.1N NaOH. The pH was adjusted to 7.5+0.1 and the final volume was made up to 1 L with water. The P021 was found to be stable (>95%) in artificial intestinal juice up to 2 hours.

P021 was expected to be BBB permeable as it is a four amino acid fragment with adamantylated glycine (enhances lipophilicity) added to the C-terminal of an 11-mer parent CNTF peptide, Peptide 6 (P6), which we previously showed to be BBB permeable (Chohan et al., 2011). The BBB studies on P021 were carried out through a commercial service (APREDICA, Watertown, Mass.). Adult mice (9-11 month old C57/Bl6) were given a single i.p. injection of 1.5 mg/0.1 mL P021/mouse. Animals were bled 10 and 30 min post injection and plasma was isolated; 10 and 30 min post injection, each animal was transcardially perfused with PBS followed immediately by the removal of the brain and its homogenization in 1 ml PBS. The brain concentrations, as analyzed by LC/MS/MS, were 28+8.5 ng/mL and 2.35+1.7 ng/mL 10 and 30 min post i.p. injection respectively. The brain:plasma ratio increased 67% from 10 to 30 min.

The homozygous 3×Tg-AD mice were obtained from Dr. Frank LaFerla (University of California, Irvine) through Jackson Laboratory (New Harbor, Me., USA). The background of the 3×Tg-AD mice is a hybrid 129/Sv×C57BL/6. Non transgenic wild type (WT) mice used were from the same strain and genetic background and were also obtained from Jackson Laboratory. Mice were housed and bred in accordance with approved protocols from our Institutional Animal Care and Use Committee (IACUC), according to the PHS Policy on Human Care and Use of Laboratory animals (revised January, 2013). This study was performed on homozygous 3×Tg-AD and WT female mice. Mice were group-housed (4 animals per cage) with a 12:12 h light/dark cycle and with ad libitum access to food and water.

The female 3×Tg-AD mice (9-10 months old) (n=15-16) and age and gender matched WT controls (n=15-16) were treated orally with P021 or vehicle diet for 12 months. Treatment was administered as 60 nmol peptide/g formulated diet (Research Diets; New Brunswick, N.J.). The vehicle-treated control animals received the same diet but without the peptide. On average, each mouse consumed ~2.7 g diet/day. Animals were behaviorally tested after 6 months of treatment (15-16 months of age). First, general behavioral battery of tests was done, and then cognitive tests were carried out. After completion of the behavioral task, half of the animals (n=7-8/group) were perfused and brain tissue was collected for immunohistochemical and biochemical analysis. Remaining animals were continued on Peptide 021/vehicle diet for another 6 months, and were sacrificed at 21-22 months of age for immunohistochemical and biochemical analysis as seen in FIG. 13. No behavioral studies were carried out in 12 month treatment/21-22 month old mice as the number of mice was small and they were too old for any reliable behavioral analysis. Besides, the main objective with the longitudinal study was to evaluate the effect of treatment on disease pathology.

The physical state and condition of the animals were carefully checked throughout the treatment by evaluating grooming, posture, physical state, and clasping reflex. Body weight, body temperature, and food consumption during the first 6 months were also recorded.

An elevated plus maze was used to evaluate anxiety/emotionality of the mice. It consisted of four arms (30×5 cm) connected by a common 5×5 cm center area. Two opposite facing arms were open (OA), whereas the other two facing arms were enclosed by 20-cm high walls (CA). The entire plus-maze was elevated on a pedestal to a height of 82 cm above floor level in a room separated from the investigator. Ambient luminosity was maintained at 60 Lux to control the anxiogenic feature of light for rodents. The mouse was placed onto the central area facing an open arm and allowed to explore the maze for a single 8 min session. Between each session, any feces were cleared from the maze, and the maze floor was cleaned with 70% alcohol to remove any urine or scent cues. For each animal, the number of CA entries, OA entries, and amount of time spent in CA and OA were automatically recorded by a video tracking system (ANY-Maze software, version 4.5, Stoelting Co., Wood Dale, Ill., USA). As OAs are more anxiogenic for rodents than CAs, the percentage of time spent in OA was calculated to evaluate anxiety-like behavior of animals. The percentage of time spent in OA corresponds to the ratio of the time spent in OA compared to the time spent in all arms (OA+CA).

Exploratory activity was evaluated by allowing mice to freely explore an open field arena for 15 min. The testing apparatus was a classic open field (i.e. a PVC square arena 50×50 cm, with walls 40 cm high). The open field was placed in a room separated from the experimenter. The open field was surmounted by a video camera connected to a computer tracking animals. Data collection was performed using a video tracking system (ANY-Maze software, version 4.5, Stoelting Co., Wood Dale, Ill., USA). The data was analyzed for time spent in the center of the arena (measure of anxiety) and distance covered (measure of exploratory activity) during the single 15-minute testing session.

Mice were tested for one-trial object recognition based on the innate tendency of the rodents to differentially explore novel objects over familiar ones, using an adaptation of the procedure previously described by Sargolini and collaborators (2003). The testing apparatus was a classic open field (i.e. a PVC square arena, 50×50 cm, with walls 40 cm high). The open field was placed in a part of the room separated from the investigator and was surmounted by a video camera connected to a computer. Three objects were employed in this task. The general procedure consisted of three different phases: a habituation phase (4 sessions of 10 min each on four consecutive days), a sample phase (5th day), and a test phase (5th day). On the first four days, mice were individually submitted each day to a familiarization session of 10 min during which they were introduced in the empty arena in order to become familiar with the apparatus. On the fifth day, each mouse was first submitted to the sample phase where two identical objects were placed in a symmetric position from the centre of the arena, and the mouse was allowed to freely explore the objects for 10 min. After a 15 minute delay during which the mouse was returned to its home cage, the animal was reintroduced in the arena to perform the test phase. During the test phase, the mouse was exposed to two objects for another 10 min: a familiar object (previously presented during the sample phase) and a new object, placed at the same location as that of other object during the sample phase. Data collection was performed using a video tracking system (ANY-Maze software, version 4.5, Stoelting Co., Wood Dale, Ill., USA). Object discrimination was evaluated by the index: [(time spent exploring the new object)/(time spent exploring both old and new objects)×100] during the test phase.

A spatial reference memory task in the Morris water maze was adapted from the procedure previously described by Morris and collaborators (1982). The procedure was performed in a 180-cm diameter circular tank. The pool was filled with water (at room temperature, 21±10 C) made opaque by adding white non-toxic paint. Acquisition started with the escape platform (14 cm in diameter submerged 1 cm below water surface) in the Northwest quadrant, and each animal was given 90 s to find the platform. If the mouse did not find the platform in 90 s, it was gently guided to it. At the end of each trial, the mouse was left on the platform for 20 s, then dried, and returned to its home cage until the next trial. Four such acquisition trials were given on each day for four consecutive days. Each animal performed a total of 16 trials corresponding to a partial training of the spatial reference memory task. The measures of learning were the time and distance covered to reach the escape platform. For the probe trial, the tank was divided into four imaginary quadrants and a small zone where the escape platform had been. The measures of retention were the percent time spent and the percent distance covered in each quadrant. Swim speed was also calculated. Mice behavior in the water-maze was monitored by a Samsung Digital Camera (SDC 4304) mounted to the ceiling and tracked and timed using a SMART (PanLab, San Diego Instruments) version 2.0.14 software.

After completion of the behavioral task at six months treatment (15-16 months old animals), half of the animals (n=7-8/group) were perfused and brain tissue was collected for immunohistochemical and biochemical analysis. Remaining animals were continued on P021/vehicle diet for another 6 months, and were sacrificed at 21-22 months of age for immunohistochemical and biochemical analysis.

Animals were anesthetized with an overdose of sodium pentobarbital (125 mg/kg) and transcardially perfused with 0.1 M phosphate buffered saline (PBS). After perfusion, the brains were removed from the skull immediately. The left hemisphere was dissected into hippocampus, cerebral cortex, cerebellum, and brain stem, immediately frozen on dry ice, and then stored at −800 C for biochemical analysis. The complete right hemisphere was immersion fixed in 4% paraformaldehyde in 0.1 M PBS for 24-48 hours followed by cryoprotection in a 30% sucrose solution at 40 C overnight. Later, the 40-µm thick sagittal sections were cut on a freezing microtome. The sections were stored in glycol anti-freeze solution (Ethylene glycol, glycerol, and 0.1 M PBS in 3:3:4 ratio) at −200 C until further processing for immunohistochemical staining.

Fluorescent staining and densitometric quantification of dendritic and synaptic markers Immunohistochemistry was performed on free-floating sections and every tenth brain section was chosen for densitometry and quantification. For immunohistochemical quantification, 5-6 brain sections of minimum 6 animals per group were analyzed for dendritic and synaptic plasticity markers. All stainings for fluorescence intensity quantification were carried out under identical conditions including all tissue samples for a particular staining processed at the same time, and similar laser and detector settings. The primary antibodies against the following proteins were used at the indicated dilution: mouse monoclonal anti-synaptophysin (1:200; Millipore, Temecula, Calif., USA), mouse monoclonal SMI 52 to MAP2 (1:1,000, Covance, Emeryville, Calif., USA), rabbit polyclonal anti-GluR1 (1:300; Millipore, Temecula, Calif., USA), rabbit monoclonal anti-GluR2/3 (1:100, Abcam, Cambridge, Mass., USA), and rabbit polyclonal anti-N-methyl d-aspartate (NMDA) receptor 1 (1:200, Thermoscientific, Rockford, Ill., USA). The following secondary antibodies were used: Alexa 488-conjugated goat anti-mouse IgG antibody (1:500, Molecular Probes, Carlsbad, Calif., USA), Alexa 488-conjugated goat anti-rabbit IgG antibody (1:500, Molecular Probes, Carlsbad, Calif., USA), Alexa 555-conjugated goat anti-rabbit IgG antibody (1:500, Invitrogen, Camarillo, Calif., USA), and CY3-conjugated goat anti-rabbit antibody (1:500, Jackson Laboratory, Maine, USA).

For densitometry, the region of interest was outlined on every tenth section in a series of 40 µm thick sagittal sections. For immunohistochemistry with synaptophysin, MAP2, GluR1, GluR2/3, and NR1, the entire area of the dentate gyrus (DG), the CA1, and the CA3 of the hippocampus were analyzed. Maximum projection images were then generated based on confocal z-stacks using Nikon 90i fluorescent microscope equipped with Nikon C1 three-laser confocal system and a Nikon DS U1 digital camera. The antibody staining was quantified by measuring mean pixel intensity (MPI) with the software Image-ProPlus 5.0 (Media Cybernetics, Silver Spring, Md., USA).

For immunohistochemical quantification of Ki-67+ cells in DG of the hippocampus, every 10th section (roughly 5-6 sections per brain) from minimum 6 animals was analyzed. Polyclonal antibody against C-terminus of Ki-67 of mouse origin (1:75, Santa Cruz Biotechnology, Santa Cruz, Calif., USA) and Alexa 555-conjugated goat anti-mouse IgG secondary antibody (1:500, Molecular Probes, Carlsbad, Calif., USA) were used. Nuclei were stained using TO-PRO-3 Iodide (1:1,000, Invitrogen, Camarillo, Calif., USA). Quantification of Ki-67+ was performed using a modified stereological method as described in the art. Briefly, labeled cells were manually quantified in the subgranular zone (SGZ) along the granule cell layer of the hippocampus using a 40× objective of a Nikon 90i fluorescent microscope. To measure the total number of cells in the entire DG, the number of positive cells was divided by the number of sections counted to obtain a mean which was then multiplied by 60, the average number of sections in the hippocampus.

For fluorescent immunohistochemical quantification of abnormally hyperphosphorylated tau, 6-7 brain sections of minimum 6 animals (from 15-16 months group) were analyzed. The phosphorylated tau antibody, mouse monoclonal AT8 which recognizes phosphorylation sites Serine 202/Threonine 205 (1:500; ThermoScientific, Rockford, Ill., USA) was used. Alexa 488-conjugated goat anti-mouse IgG antibody (1:500, Molecular Probes, Carlsbad, Calif., USA) was used as secondary antibody. Only brain regions showing overt positive specific staining, namely the CA1 of the hippocampus and the subiculum, were quantified. Maximum projection images of high-magnification fields were generated as described above. The AT8 immunoreactive neurons were quantified as described in the art. Briefly, images were filtered with a predetermined threshold using NIH Image J (v.1.46r) to create a binary image identifying positive and negative immunolabeling. The AT8 immunoreactive load was calculated as the percentage of area occupied by immunoreactive label. Mean load values were averaged from 2-3 non-overlapping representative fields from hippocampus CA1 and subiculum in 6-7 separate sections per animal.

TS+ plaque load was quantified on every 10th section (roughly 6-7 sections per set) of minimum 6 animals from both 15-16 months old and 21-22 months old groups. A modified thioflavin-S staining protocol was used as follows. Free floating brain sections were washed in large volumes of distilled water and were then incubated in 0.25% KMnO4 for 4-5 minutes, washed with water, and then treated with a solution of 1% K2S2O5 and 1% oxalic acid for 40-60 seconds until the brown color was completely washed out. Sections were then incubated with 0.05% thioflavin-S in water in the dark for 8 minutes followed by differentiation in 80% ethanol twice for 1 minute each. Sections were then washed 3 times in distilled water for 1 minute each and mounted and coverslipped using Fluorgel mounting medium (electron microscopy sciences, PA<USA). The images were taken using Nikon 90i fluorescent microscope, thresholded using Image J (v.1.46r) and TS+ plaque load was quantified in hippocampus CA1 and subiculum.

The tissue from left cerebral hemisphere stored at −800 C from each mouse was homogenized in a Teflon-glass homogenizer to generate 10% (w/v) homogenate. The pre-chilled homogenization buffer contained 50 mM Tris-HCl (pH 7.4), 8.5% sucrose, 2 mM EDTA, 2 mM EGTA, 10 mM b-mercaptoethanol plus the following protease and phosphatase inhibitors: 0.5 mM AEBSF, 10 µg/ml aprotinin, 10 µg/ml leupeptin, 4 µg/ml pepstatin, 5 mM benzamidine, 20 mM b-glycerophosphate, 50 mM sodium fluoride, 1 mM sodium orthovanadate, and 100 nM okadaic acid. Protein concentration of each brain homogenate was determined by modified Lowry assay. The tissue homogenates were boiled in Laemmli's buffer for 5 min, and then subjected to 10% or 12% SDS-polyacrylamide gel electrophoresis followed by transfer of separated proteins on 0.45 µm Immobilon-P membrane (Millipore, Bedford, Mass., USA). The blots were developed with antibodies to BDNF and GSK3β [rabbit polyclonal anti-BDNF, N-20 (1:500, Santa Cruz Biotechnology, Santa Cruz, Calif., USA), rabbit monoclonal anti GSK3β (1:1000, Cell Signaling, Danvers, Mass., USA), and rabbit polyclonal anti-phosphoGSK3β, Ser9 (1:1000, Cell Signaling, Danvers, Mass., USA)]; antibodies to total tau and phospho-tau [rabbit polyclonal R134D, total tau (1:5,000), mouse monoclonal 43D, total tau (0.5 µg/mL), rabbit polyclonal pS199, phosphorylation site Serine 199 (1:2,000, Invitrogen, Grand Island, N.Y., USA), mouse monoclonal PHF-1, phosphorylation sites Serine 396/Serine 404 (1:1,000, kind gift from Dr. Peter Davies, Albert Einstein School of Medicine, NY, USA), mouse monoclonal 12E8, phosphorylation sites Serine 262/Serine 356 (1:1,000, kind gift from Dr. Dale Schenk, Elan Pharmaceuticals, San Francisco, Calif., USA), and mouse monoclonal AT8, phosphorylation sites Serine 202/Threonine 205 (1:1,000, ThermoScientific, Rockford, Ill., USA)]; and antibodies to glutamate receptors' subunits [rabbit polyclonal anti-GluR1 (1:1,000, Millipore, Temecula, Calif., USA), rabbit monoclonal anti-GluR2/3 (1:2,000, Abcam, Cambridge, Mass., USA), and rabbit polyclonal anti-N-methyl d-aspartate (NMDA) receptor 1 (1:500, Thermoscientific, Rockford, Ill., USA)]. The corresponding horseradish peroxidase-conjugated secondary antibodies were used. For loading control, the blots were developed with rabbit polyclonal antibody to GAPDH (1:1,000, Santa Cruz Biotechnology, Santa Cruz, Calif., USA). Immunoreactive protein bands were visualized with enhanced chemiluminescence (ECL) reagents (Pierce, Rockford, Ill., USA). The ECL films of the blots were scanned and analyzed using Multi Gauge software version 3.0 (Fujifilm, Tokyo, Japan). For quantification of different markers, each immunoreactive band was normalised to it's corresponding GAPDH band and then they were grouped together for comparison across different genotype and treatment groups.

ELISA quantification of Aβ load in the brain tissue was performed using total human (Hu) Aβ40 and Aβ42 measurements by ELISA. The cerebral cortex from both 15-16 months old and 21-22 months groups were homogenized in 10 volumes of ice-cold guanidine buffer (5.0 M guanidine-.HCl, 50 mM Tris. C1, pH 8.0). The homogenates were mixed for 4 hours at room temperature, and stored at −80° C. For enzyme-linked immunosorbant assay (ELISA) analysis, the brain homogenates were diluted 1:25 (for Hu Aβ40 and Aβ42) for 15-16 months old mice or 1:50 for Hu Aβ40 and 1:75 Hu Aβ42 for 21-22 months old mice with ice-cold reaction buffer [5% BSA, 0.03% Tween-20, 2.1 mM AEBSF, 20 µg/ml aprotinin, 20 µg/ml leupeptin, 2.0 mM EDTA, pH 7.4 in DPBS (Thermo scientific, Product #28344)] and centrifuged at 16,000×g for 20 min at 4° C. The supernatant was further diluted 1:1 (v/v) with standard diluent buffer, assessed using ELISA kit specific for Hu Aβ40 (Invitrogen, Grand Island, N.Y., USA, Cataaog #KHB3482) and Hu Aβ40 (Invitrogen, Grand Island, N.Y., USA, Catalog #KHB3442), and calibrated with synthetic Aβ peptides from Invitrogen according to the manufacturer's instructions. The Aβ40 peptide standards were prepared with the same composition of buffers used for the diluted samples.

Soluble Hu Aβ40 measurements were performed by ELISA. The cortex from both 15-16 months old and 21-22 months groups were homogenized in 20 volumes of ice-cold Tris-saline buffer (T5030, Sigma, 50 mM Tris-HCl, 150 mM NaCl) containing complete protease inhibitor cocktail (Roche). Homogenates were centrifuged at 100,000×g for 1 h at 4° C. The Tris-saline supernatant was diluted 1:1 for 15-16 months old group or 1:5 for 21-22 months old group with standard diluent buffer supplied in the kit and assessed using ELISA kit specific for Hu Aβ40 (Invitrogen, Grand Island, N.Y., USA, Catalog #KHB3482) and calibrated with synthetic Aβ peptides from Invitrogen according to the manufacturer's instructions. The Aβ40 peptide standards were prepared with the same composition of buffers used for the diluted samples.

To confirm the mechanism of action of P021 through enhanced BDNF induced decrease in GSK3β activity, primary neuronal cell cultures from embryonic day 18 (E18) mouse cortex were employed. Primary neuronal cultures were prepared from C57BL/6 mice using the procedure in the art. Briefly, C57BL/6 time pregnant E18 female mice from Charles River labs were anesthetized and killed by cervical dislocation. All studies were performed in accordance with the recommendations in the Guide for the Care and Use of Laboratory Animals of the National Institutes of Health (NIH). The protocol was approved by the Institutional Animal Care and Use Committee (IACUC) of the New York State Institute for Basic Research in Developmental Disabilities (Protocol no. 199). All surgeries were performed under anesthesia, and all efforts were made to minimize suffering. Embryos were removed and placed in cold hibernate A (Brain bits, Springfield, Ill., USA), and all following steps were performed in ice-cold hibernate A, under the stereoscopic (dissection) microscope placed in a laminar flow hood. Fetal brains were removed carefully; cortex was separated, and was dissected and cut into small pieces using microsurgical scissors. The cut tissue was transferred with number 5 forceps to 15 ml tubes containing 0.1% trypsin in versene (Invitrogen Life Technologies, Grand Island, N.Y., USA) and incubated for 15 min at 37° C. followed by inactivation with 10% fetal bovine serum (FBS) in Neurobasal complete medium (Neurobasal Medium supplemented with 2×B-27, 0.30% glutamine, and penicillin/streptomycin 0.1 mg/ml and 0.1 U/ml respectively). After 72 hours, the medium was replaced and supplemented with fresh medium with different treatments as described below. All medium components were purchased from Invitrogen Grand Island, N.Y., USA. Cells were maintained in an incubator at 37oC at 5% CO2/95% atmospheric air.

The cells were cultured for 72 hours prior to treating with P021-specific BDNF-TrkB-PI3-kinase/GSK3β pathway inhibitors. Initially, a time course experiment was done to determine the effect of P021 on BDNF expression. On day-in-vitro (DIV) 4, culture medium was replaced with fresh medium containing P021 in a final concentration, 1 µM. The effect of P021 on BDNF expression was evaluated after 1 hr, 3 hrs, 6 hrs, and 24 hrs of treatment in two separate set of experiments. In later experiments, specific pharmacological inhibitors were used in the following concentrations for the specified times of pre-incubation before P021 treatment: K252a (Calbiochem/EMD, Billerica, Mass., USA), Trk receptor inhibitor, 200 nM for 1 hr; wortmannin (Calbiochem/EMD, Billerica, Mass., USA), PI3-kinase inhibitor, 100 nM for 20 min; and LiCl (Sigma-Aldrich, St Louis, Mo., USA), a GSK3β inhibitor, 20 mM for 10 min. Based on the initial evaluation of the effect of P021 on BDNF expression, GSK3β activity, and abnormally hyperphosphorylated tau levels, all biochemical studies with pharmacological inhibitors were performed on cultured neurons 6 hours after P021 treatment (with specific inhibitor pre-treatment). All experiments were done on primary cultured neurons seeded in 12-well plates at a density of 6×10⁵ cells/well.

Following treatment, cells were washed 2 times in glucose buffered saline, GBS (5.4 mM KCl, 138 mM NaCl, 22 mM glucose, and 2 mM Na—KPO4 pH 7.2), and then lysed by 5 min incubation on ice in 100 or 150 µl of ice-cold RIPA buffer (PBS, 1% w/v NP-40 from Fisher Scientific, 0.1% w/v SDS, and 0.5% w/v sodium deoxycholate) containing 1 mM AEBSF (Gold Biotechnology, St. Louis, Mo., USA), 10 µg/ml aprotinin (Sigma-Aldrich, St. Louis, Mo., USA), and 20 µg/ml of leupeptin and pepstatin (US Biochemicals, Cleveland, Ohio, USA), and phosphatase inhibitors: NaF, Na orthovanadate, β-glycerophosphate, and microcystein (Sigma-Aldrich, St. Louis, Mo., USA). Extracts were prepared by collecting and pooling a minimum of 2 wells by scraping, and lysates were centrifuged at 20,000×g for 10 min at 4° C. Protein concentration of each cell lysate was determined using the BCA kit (Thermo Scientific, Rockford, Ill., USA). The Western blots were performed as described above for BDNF, pGSK3β (pSer9), GSK3β, and abnormally hyperphosphorylated and total tau.

Statistical analyses were conducted using SPSS version 17.0 (© SPSS Inc., 1989-2007, Chicago, Ill., USA), SASv5 software (SAS Institute, Cary, N.C., USA), and GraphPad Prism version 5.0 (GraphPad software inc., La Jolla, Calif., USA). Data are presented as mean±S.E.M. The normality of the data was determined using Kolmogorov-Smirnov test. For analysis involving multiple groups, one-way ANOVA with post hoc Bonferroni's/Fischer's/Newman-Keul's test (as indicated) was used. For all other comparisons (including inter-group comparisons for genotype/treatment effect), Student's t-test was used. For skewed distributions, Mann-Whitney U test was used for comparison of means. Grubb's test was used to identify the statistically significant outliers in all data sets. For all purposes, $p<0.05$ was considered as statistically significant.

The results indicated that P021 treatment reduces tau pathology both at moderate and severe stages of the disease in 3×Tg-AD mice. Tau is a neuronal microtubule-associated protein which plays a role in microtubule assembly, stabilization, and axonal transport. In AD and related tauopathies, there is abnormal hyperphosphorylation of tau which leads to reduced binding of tau to microtubules, and subsequent accumulation as neurofibrillary tangles and neurodegeneration (Grundke-Iqbal et al., 1986; 1988). In 3×Tg-AD mice, the tau pathology occurs at around 12 months and is first visible in the CA1 pyramidal neurons and subiculum, becoming readily apparent in the hippocampus and in cortical structures several months later. The effect of chronic oral treatment with P021 on tau pathology was evaluated both at 15-16 months and 21-22 months of age in these mice, as seen in FIG. 13.

Using immunohistochemical quantification, the level of abnormally hyperphosphorylated tau was evaluated in the hippocampus from both 15-16 month and 21-22 month old mice employing a phospho-specific antibody, AT8, which recognizes abnormally hyperphosphorylated tau at Ser202/Thr205 as seen in FIG. 14A-D. AT8 immunoreactivity load corresponding to neurofibrillary tangle pathology was markedly evident in CA1 and subiculum regions of the hippocampus in 3×Tg-AD mice. A significant reduction in AT8 immunoreactive load was observed in P021 treated 3×Tg-AD mice compared to the vehicle treated group as seen in FIG. 14A-D; 15-16 month old animals, CA1, Student's t-test, p=0.0022, subiculum, Student's t-test, p=0.0004; 21-22 month old animals, CA1, student's t-test, p=0.06, subiculum, Student's t-test, p=0.037).

We found a significant increase in abnormal hyperphosphorylation of tau at Ser396/Ser404 in 21-22 month old vehicle treated 3×Tg-AD mice as compared to WT by Western blots developed with monoclonal antibody, PHF-1 (FIGS. 33E&F; ANOVA, p=0.0023, Bonferroni's post-hoc test, p<0.05, Student's t-test, p=0.0345); chronic treatment with P021 significantly reduced the abnormal hyperphosphorylation at this site in both 3×Tg-AD mice (Bonferroni's post-hoc test, p<0.05, Student's t-test, p=0.0382) and WT animals (Bonferroni's post-hoc test, p<0.05, Student's t-test, p=0.0066). Similarly, Western blots developed with monoclonal antibody 12E8 that recognizes pSer262/pSer356 sites showed a significant increase in 21-22 month old vehicle treated 3×Tg-AD mice compared to WT controls (FIGS. 33E&F; ANOVA, p=0.005, Bonferroni's post-hoc test, p<0.05, Student's t-test, p=0.0084) and P021 treatment significantly reduced the hyperphosphorylation of tau at these sites in 3×Tg-AD mice (Bonferroni's post-hoc test, p<0.05, Student's t-test, p=0.0306). A significant increase in the abnormal hyperphosphorylation of tau was also observed at pSer199 in 21-22 month old vehicle treated 3×Tg-AD mice compared to WT (FIGS. 14E&F; ANOVA, p=0.108, Bonferroni's post-hoc test, p>0.05, Student's t-test, p=0.024) but not in the Peptide 021 treated 3×Tg-AD mice (Bonferroni's post-hoc test, p>0.05 Student's t-test, p=0.2326).

We confirmed the expression of human tau in 3×Tg-AD mice by employing Western blots from hippocampi of 21-22 month old animals using human specific tau antibody, 43D. As expected, human tau expression was found only in 3×Tg-AD mice; no significant effect of P021 on the level of expressed human tau was noted (FIGS. 14E&F; Student's t-test, p=0.5344). We determined if P021 treatment had any effect on the expression level of total tau by employing a pan-tau polyclonal antibody, R134d. The Western blots developed with R134d did not reveal any significant effect of P021 on the total tau level (FIGS. 14E&F; ANOVA, p=0.078; WT-Vh vs WT-P021, Bonferroni's post-hoc test, p>0.05, Student's t-test, p=0.5761; Tg-Vh vs Tg-P021, Bonferroni's post-hoc test, p>0.05, Student's t-test, p=0.0896). However, an increased expression of total tau in 3×Tg-AD mice was observed (pooled WT vs Tg, Student's t-test, p=0.0041).

P021 treatment was also found to attenuate soluble but not aggregated Aβ at moderate stage of the pathology in 3×Tg-AD mice. In AD, Aβ deposition proceeds from oligomers to diffuse plaques and ultimately the formation of compact plaques which can be identified as thioflavin S (TS)-positive plaques. 3×Tg-AD mice first show the presence of intraneuronal Aβ in neocortical regions by 3-4 months of age and subsequently in CA1 pyramidal neurons by 6 months. Extracellular Aβ plaques become readily evident in hippocampus and cortical regions by nearly 12 months of age. To evaluate the effect of chronic treatment with P021 on Aβ pathology, we examined the Aβ load in the hippocampus and cortex of P021 and vehicle treated 3×Tg-AD mice (FIG. 15).

Quantification of soluble and insoluble Aβ1-40 and Aβ1-42 by ELISA in the cortex of 3×Tg-AD mice showed a trend of large animal to animal variation. Nonetheless, we found a significant reduction with P021 treatment in both soluble Aβ1-40 and Aβ1-42 in 15-16 month old 3×Tg-AD mice (FIG. 15A; Soluble Aβ1-40, Tg-Vh vs Tg-P021, Student's t-test, p=0.0049; Soluble Aβ1-42, Tg-Vh vs Tg-P021, Student's t-test, p=0.0235). In 21-22 month old 3×Tg-AD mice, both soluble Aβ1-40 and Aβ1-42 were not significantly reduced by P021 treatment (FIG. 15A; Soluble Aβ1-40, Tg-Vh vs Tg-P021, Mann-Whitney U test, p=0.7308; Soluble Aβ1-42, Tg-Vh vs Tg-P021, Student's t-test, p=0.3328). The levels of both insoluble Aβ1-40 and Aβ1-42 did not show any significant effect of P021 treatment either in 15-16 month or 21-22 month old mice (FIG. 15B; 15-16 month old mice, Insoluble Aβ1-40, Tg-Vh vs Tg-P021, Student's t-test, p=0.7514, Insoluble Aβ1-42, Tg-Vh vs Tg-P021, Student's t-test, p=0.2529; 21-22 month old mice, Insoluble Aβ1-40, Tg-Vh vs Tg-P021, Student's t-test, p=0.4503, Insoluble Aβ1-42, Tg-Vh vs Tg-P021, Student's t-test, p=0.4757).

Quantification of thioflavin-S (TS+) stained compact plaques showed a trend towards reduction in P021-treated 15-16 month old 3×Tg-AD mice in the CA1 region of the hippocampus (FIGS. 15C&D; 15-16 month old animals, Tg-Vh vs Tg-P021, Student's t-test, p=0.0868). However, no significant effect of the P021 treatment was found in the CA1 region in 21-22 month old mice and in the subiculum of either 15-16 or 21-22 month old mice (FIG. 15C-F; 15-16 month old mice, subiculum, Tg-Vh-vs Tg-P021, Student's t-test, p=0.7144; 21-22 month old mice, CA1, Tg-Vh vs Tg-P021, Student's t-test, p=0.1757, subiculum, Tg-Vh vs Tg-P021, Student's t-test, p=0.6726).

P021 treatment increases BDNF expression and decreases GSK3β activity via TrkB/PI3-kinase/AKT pathway: possible mechanism of reduction in tau and Aβ pathologies Brain derived neurotrophic factor plays an essential role in synaptic remodeling associated with memory. Survival of new born neurons in adult DG has been shown to require BDNF signaling pathway. BDNF pathway is known to be down regulated in AD. As noted above, the parent CNTF peptide, P6, from which P021 is derived, increased the BDNF mRNA expression in the hippocampus in an experimental rat model of sporadic AD. P021 can also increase BDNF expression in both hippocampus and cortex of aged rats. Also, previously neurotrophins have been shown to induce BDNF expression through glutamate receptor pathway. BDNF acting via tyrosine kinase B (TrkB) receptor has been reported to reduce tau phosphorylation via phosphoinositide 3 (PI-3) kinase/AKT (protein kinase B)/glycogen synthase kinase (GSK)3β pathway. Previously, increasing the BDNF expression by different strategies has been shown to decrease tau pathology via a decrease in the activity of GSK3β in animal models of AD. GSK-3β is also known to mediate Aβ induced neuritic damage in AD and impairment of spatial memory and LTP; the GSK3α isoform regulates APP processing and Aβ production. GSK3β inhibitors have been shown to reduce both tau and Aβ pathologies and rescue cognitive impairment in AD mouse models. BDNF has also been shown to reduce amyloidogenic processing by reducing Sorting protein-related receptor with A-type repeats (SORLA) gene expression. Nonetheless, it is prudent to mention that direct BDNF treatment has also been shown to exert no effect on Aβ pathology in AD transgenic mouse models. Thus, an investigation was performed into the possibility whether the robust reduction in tau pathology and a trend towards reduction in Aβ pathology by P021 treatment was mediated through BDNF and GSK3β pathways (FIG. 16).

Western blots of hippocampus developed with anti-BDNF antibody revealed a significant reduction in BDNF expression in 3×Tg-AD mice which was rescued by P021 treatment in 15-16 month old animals (FIGS. 16A&B; ANOVA, p=0.0014, WT-Vh vs Tg-Vh, Bonferroni's post hoc test, p<0.01, Student's t-test, p=0.0016; Tg-Vh vs Tg-P021, Bonferroni's post-hoc test, p<0.05, Student's t-test, p=0.0377). In 21-22 month old animals, BDNF expression was decreased in 3×Tg-AD mice as compared to WT mice but the difference did not reach statistical significance (FIGS. 16C&D; ANOVA, p=0.0136, Bonferroni's post hoc test, p>0.05, Student's t-test, p=0.1517). However, P021 induced a significant increase in BDNF expression in 3×Tg-AD mice (FIGS. 16C&D; Bonferroni's post hoc test, p<0.05, Student's t-test, p=0.0045).

GSK3β is a major tau serine/threonine kinase which phosphorylates tau at many different sites including Ser199, Ser202, Thr205, Ser396, and Ser404 evaluated in the current study. GSK3β is one of the downstream effectors of PI3-K/AKT signal transduction pathway and can be inhibited by AKT-mediated phosphorylation on Ser9. Thus, an investigation into the effect of P021 mediated increase in BDNF on phosphorylation of GSK3β at Ser9 in 3×Tg-AD mice was performed. A significant decrease in Ser9 phosphorylated GSK3β (inactive form) was found in 3×Tg-AD mice compared to WT mice both in 15-16 month old and 21-22 month old animals (FIG. 16A-D; 15-16 month old group, ANOVA, p=0.0064, WT-Vh vs Tg-Vh, Bonferroni's post-hoc test, p<0.05, Student's t-test, p=0.0029; 21-22 month old group, ANOVA, p=0.05, WT-Vh vs Tg-Vh, Bonferroni's post-hoc test, p<0.05, Student's t-test, p=0.0096). Chronic treatment with P021 significantly increased Ser9 phosphorylated GSK3β (inactive form) in 3×Tg-AD mice both in 15-16 month old and 21-22 month old animals (FIG. 6A-D; 15-16 month old group, Tg-Vh vs Tg-P021, Bonferroni's post-hoc test, $p<0.05$, Student's t-test, $p=0.0306$; 21-22 month old group, Tg-Vh vs Tg-P021, Bonferroni's post-hoc test, $p<0.05$, Student's t-test, $p=0.0321$).

These results provided the mechanistic details of the effect of P021 and suggested that decrease in tau and Aβ pathologies after chronic treatment with P021 in 3×Tg-AD mice could be due to increased BDNF expression mediated AKT-induced inhibition of GSK3β activity. To further evaluate this hypothesis, we treated E18 primary cultured cortical neurons with P021 (1 μM) and analyzed the effect on BDNF expression and GSK3β activity (FIG. 16E-N). P021 induced a significant increase in BDNF expression in cultured neurons 6 hrs and 24 hrs after treatment (FIGS. 16E&F; Control vs P021 treated neurons; 6 hrs, Student's t-test, $p=0.0252$, 12 hrs, Student's t-test, $p=0.0041$). After 6 hrs of treatment with P021, a significant decrease in GSK3β activity was observed, i.e. increased phosphorylation of GSK3β at Ser9 (FIGS. 16G&H; Student's t-test, $p<0.0001$). As expected, a significant decrease in abnormal hyperphosphorylation of tau was observed at several sites 6 hrs after P021 treatment (FIGS. 16G&H; AT8, pSer202/PThr205, Student's t-test, $p=0.0062$; PHF-1, pSer396/pSer404, Student's t-test, $p=0.0033$; 12e8, pSer262/pSer356, Student's t-test, $p=0.0545$). No effect of P021 treatment was observed on expression levels of total tau (FIGS. 16G&H; R134d, pan-tau antibody, Student's t-test, $p=0.2206$).

To further investigate the role of TrkB/PI3-kinase/AKT/GSK3β pathway in P021 mediated decrease in abnormally hyperphosphorylated tau, we used specific pharmacological inhibitors of this signaling pathway. In the presence of K252a, a selective Trk receptor inhibitor, P021 failed to exert any effect on abnormal hyperphsoprylation of tau as evaluated by AT8 immunoblotting (FIGS. 16I&J; P021 vs P021+K252a, Bonferroni's posthoc test, $p<0.01$, Student's t-test, $p=0.0056$). Similar effect was observed in the presence of PI3-kinase inhibitor, wortmannin (FIGS. 16K&L; P021 vs P021+wortmannin, Bonferroni's posthoc test, $p<0.001$, Student's t-test, $p<0.0001$). To further confirm that P021 mediated enhanced BDNF expression induced decrease in abnormal hyperphosphorylation of tau was via GSK3β inhibition, we pre-treated primary cultured neurons with lithium, a GSK3β inhibitor. We found that P021 was unable to decrease the abnormal hyperphsophorylation of tau when GSK3β activity was already inhibited in the presence of lithium (FIGS. 16M&N; P021 vs P021+Licl, Bonferroni's posthoc test, $p>0.05$, Student's t-test, $p=0.209$).

The present invention also involves the finding that P021 treatment enhances dentate gyrus neurogenesis in 3×Tg-AD mice. In a previous study, the subcutaneous administration of P021 was found to be able to enhance DG neurogenesis by inhibition of LIF signaling pathway in normal adult C57Bl6/J mice. Thus, an investigation was performed into the effect of chronic oral treatment with P021 on neurogenesis in 15-16 month old (6 months treated) 3×Tg-AD mice by immunostaining for Ki-67, a cell proliferation marker which has been demonstrated to effectively measure early stage of neurogenesis. As expected, the number of Ki-67+ cells in the DG of vehicle treated 3×Tg-AD mice was significantly reduced as compared to WT mice (FIGS. 17A&B; ANOVA, $p=0.0007$; WT-Vh vs Tg-Vh, Bonferroni's post-hoc test, $p<0.001$, Student's t-test, $p<0.0001$). Remarkably, P021 treated 3×Tg-AD mice revealed a significantly increased Ki-67+ cells in the DG of the hippocampus compared to vehicle treated 3×Tg-AD mice (FIGS. 17A&B; Tg-Vh vs Tg-P021, Bonferroni's post-hoc test, $p<0.05$, Student's t-test, $p=0.0387$). These data demonstrate that cell proliferation (an early marker of neurogenesis) was markedly impaired in aged 3×Tg-AD mice and P021 treatment rescued it to the level of WT controls. In addition to the inhibition of LIF signaling pathway, the neurogenic effect of P021 was also probably due to the increase in the expression of BDNF which has been shown to be essential for the survival of new born neurons in DG of the hippocampus.

P021 treatment was also found to rescue deficits in dendritic and synaptic plasticity markers in 3×Tg-AD mice. In AD, synaptic loss, as reflected by alterations in the expression levels of dendritic and synaptic markers, is known to correlate better with cognitive decline than either Aβ plaque load or neurofibrillary tangles. Quantitative evaluation of AD brains within 2-4 years after the clinically diagnosed disease has revealed a 25-35% decrease in density of synapses and a 15-35% loss in the number of synapses per neuron in the frontal and temporal cortices. The extent of synaptic loss is even more profound in the hippocampus where it amounts to 44-55%. 3×Tg-AD mice have been shown to exhibit deficits in dendritic and synaptic plasticity by 6 months of age, including impairments in long-term potentiation (LTP) and paired-pulse facilitation. As a result, chronic treatment with P021 in diet was studies to see whether the compound can reverse deficits in markers of dendritic and synaptic plasticity in these mice at moderate to severe stage of the disease.

Microtubule associated protein 2 (MAP2), the most widely used dendritic marker, is present in the somata and dendrites of differentiated mature neurons. It is a cytoskeletal protein involved in microtubule assembly and stabilization of dendrites which are important steps in neurogenesis and neuronal maturation. A significant decrease of MAP2 immunoreactivity was found in 3×Tg-AD mice treated with vehicle when compared to WT mice in CA1 (Bonferroni's post hoc test, $p<0.001$), CA3 (Bonferroni's post hoc test, $p<0.01$), and DG (Bonferroni's post hoc test, $p>0.05$, Student's t-test, $p=0.0421$) regions of the hippocampus (FIGS. 18A&B). In 3×Tg-AD mice treated with P021, the MAP2 immunoreactivity in CA1, CA3, and DG was significantly increased as compared to the 3×Tg-AD mice treated with vehicle diet (FIGS. 18A&B; CA1, Bonferroni's post hoc test, $p<0.001$, CA3, Bonferroni's post hoc test, $p<0.05$, and DG, Bonferroni's post hoc test, $p>0.05$, Student's t-test, $p=0.0401$).

Synaptophysin is a glycoprotein of pre-synaptic vesicles involved in the vesicle trafficking machinery by regulating synaptic vesicle exocytosis. A significant decrease of synaptophysin immunoreactivity was observed in 3×Tg-AD mice treated with vehicle compared to WT controls in CA1 (Bonferroni's post-hoc test, $p<0.001$), CA3 (Bonferroni's post-hoc test, $p<0.001$), and DG (Bonferroni's post-hoc test, $p<0.001$) (FIGS. 18C&D). P021 treatment was able to rescue the deficit in these hippocampal regions in the 3×Tg-AD mice (FIGS. 18C&D; Bonferroni's post-hoc test, $p<0.05$, $p<0.05$, and $p<0.05$ for CA1, CA3, and DG regions respectively).

Synaptic pruning is a feature of AD pathology. The expression levels of postsynaptic ionotropic glutamate receptors i.e. AMPA (α-amino-3-hydroxy-5-methyl-4-isoxazole propionic acid) and NMDA (N-methyl-D-aspartate) receptors, was evaluated due to their known essential roles in synaptic transmission and LTP as well as cellular mechanisms which are connected with learning and memory. Also, recent evidence suggests that there is a chronology of synaptic failure in AD; postsynaptic loss occurs after advanced Aβ and tau pathology and is not an early event. P021 treatment significantly increased the expression of GluR1 subunit of the AMPA receptor in the DG region of the hippocampi of 3×Tg-AD mice which showed deficit as compared to WT (FIGS. 19A&B; ANOVA, p<0.0001; WT-Vh vs Tg-Vh, Bonferroni's post-hoc test, p<0.001; Tg-Vh vs Tg-P021, Bonferroni's post-hoc test, p<0.001). Western blot quantification further confirmed the positive effect of P021 on GluR1 expression in the hippocampus of 3×Tg-AD mice (FIGS. 19C&D; ANOVA, p=0.0035; Tg-Vh vs Tg-P21, Bonferroni's posthoc test, p<0.05, Student's t-test, p=0.018). Immunohistochemical staining revealed a decrease in the density of the NMDA receptor subunit NR1-positive neurons in the CA1 (FIGS. 19A&B; ANOVA, p=0.0781, Bonferroni's post hoc test, p<0.01) and in the CA3 (FIGS. 19A&B, ANOVA, p=0.0779, Bonferroni's post-hoc test, p>0.05, Student's t-test, p=0.0472) regions of the hippocampus in 3×Tg-AD mice compared to WT mice. Treatment with P021 improved the density of NR1 expression in both CA1 and CA3 in 3×Tg-AD mice (FIGS. 19A&B; CA1, Bonferroni's post-hoc test, p>0.05, Student's t-test, p=0.046; CA3, Bonferroni's post-hoc test, p>0.05, Student's t-test, p=0.063, marginal significance). However, P021 treatment could not ameliorate the deficit in GluR2/3 density in the DG region of the hippocampus of 3×Tg-AD (FIGS. 19A&B; ANOVA, p<0.0001; WT-Vh vs Tg-Vh, Bonferroni's post-hoc test, p<0.001, Tg-Vh vs Tg-P021, Bonferroni's post-hoc test, p>0.05). Western blot analysis of the NR1 and GluR2/3 expression in hippocampus of 3×Tg-AD mice did not show any effect of P021 treatment (FIGS. 19C&D; NR1, ANOVA, p=0.0984, GluR2/3, ANOVA, p=0.3719).

Over the past decade, a general consensus has emerged that LTP is mediated by synaptic insertion of GluR1 subunit containing AMPA receptors as LTP and short-term working memory are impaired in GluR1 knockout mice, but is normal in GluR2/3 double knockouts. The positive effect of P021 on GluR1 expression (in addition to NR1 expression) in the absence of any effect on GluR2/3 expression should be sufficient for the induction of synaptic plasticity and beneficial effect on learning and memory. Nonetheless, this remains questionable based on the recent finding that LTP requires a reserve pool of glutamate receptors independent of subunit type.

P021 treatment reverses learning and memory impairment in 3×Tg-AD mice. It is widely reported that in AD patients, during initial phases of the disease, the clinical symptoms include memory loss, particularly of recent events. Neuronal and synaptic plasticity are the key factors in neuronal firing, neuronal recruitment into information-processing networks, and ultimately learning and memory mechanisms. Based on the amelioration of synaptic density deficit with P021 treatment in 3×Tg-AD mice, we speculated that cognitive deficits may also be attenuated. In 3×Tg-AD mice, the onset of cognitive impairment is known to occur around 5 months of age, in advance of overt plaque and tangle pathologies, and consists of hippocampus dependent impairment of spatial memory retention. A recent study has shown episodic memory deficit by using What-Which-Where location task (requires integration of object location and contextual cues) in 3×Tg-AD mice compared to WT mice at a much younger age i.e. 3 months. To test whether treatment with P021 can alleviate cognitive deficits in 3×Tg-AD mice, we performed a test for episodic short-term memory and a test for hippocampal-dependent spatial reference memory using one-trial object recognition/discrimination and Morris water maze tasks, respectively, at 15-16 months of age (after 6 months of P021 treatment).

The one-trial object recognition task is thought to critically depend on the entorhinal cortex, hippocampus and frontal cortex. During the sample phase, all animals similarly explored both objects (FIG. 20A; ANOVA, p>0.999). During the test phase, 3×Tg-AD mice displayed a significantly lower discrimination score than other groups (FIG. 20B; ANOVA, p=0.0023; WT-Vh vs Tg-Vh, Bonferroni's post hoc test, p<0.05, Student's t-test, p=0.0022; WT-P021 vs Tg-Vh, Bonferroni's post hoc test, p<0.05, Student's t-test, p=0.0029; Tg-Vh vs Tg-P021, Bonferroni's post hoc test, p<0.01, Student's t-test, p<0.0001). These results suggest that 3×Tg-AD mice treated with vehicle did not preferentially explore the novel object. This null preference did not reflect a lack of interest for novelty but rather enhanced attraction for familiarity. This revealed that familiar-object representation was yet to be built and finalized; therefore less attention was paid to the novel object. In contrast, WT control mice and 3×Tg-AD mice treated with P021 displayed a clear preference for the novel object. This suggested that the representation of the familiar object started to be encoded, and then was less a subject of attention at the expense of the novel stimulus. These results showed that P021 can rescue short-term memory of 15-16 month old 3×Tg-AD mice.

The spatial reference memory task assesses hippocampus dependent reference memory in rodents, requiring that mice use a spatial navigational strategy to find a fixed submerged escape platform. The hippocampal system processes information about the relationships among distal environmental cues into a spatial map where spatial coordinates of the submerged platform are encoded. The hippocampus is also crucial for memory storage, consolidation, and restitution of the spatial information.

The first parameter considered in the water-maze training was the swim speed of animals. It is indeed crucial to first elucidate if locomotivity was comparable between 3×Tg-AD and WT mice otherwise interpretation of data for learning and memory evaluation can be misinterpreted. All four groups of animals displayed similar swim speed (FIG. 20C; ANOVA, p<0.0955). We therefore analyzed performance of the animals as latency to reach the submerged platform. A significant difference of learning among groups was observed (FIG. 20D; ANOVA, p=0.010). Post-hoc analysis showed that 3×Tg-AD mice needed significantly longer latencies to reach the platform than WT control animals and 3×Tg-AD mice treated with P021 (FIG. 20D; WT-Vh vs Tg-Vh, Fisher's post-hoc test, p<0.0064, WT-P021 vs Tg-Vh, Fisher's post-hoc test, p=0.0066, Tg-Vh vs Tg-P021, Fisher's post-hoc test, p=0.0036). These results show that treatment with P021 can alleviate impairment of spatial learning in 15-16 month-old 3×Tg-AD mice.

The probe trial allows evaluating the strength of the encoding of the spatial information. The more an animal searches for the platform in the target quadrant, the more the information of the spatial coordinates of the submerged platform was strongly encoded. 3×Tg-AD mice treated with vehicle spent significantly less time in the target quadrant than WT mice treated with vehicle (FIG. 20E; Bonferroni's post-hoc test, p>0.05, Student's t-test, p=0.032). 3×Tg-AD mice treated with P021 displayed a trend towards better performance than 3×Tg-AD mice treated with vehicle, nonetheless, the difference was not statistically significant (FIG. 20E, Bonferroni's post-hoc test, p>0.05, Student's t-test, p=0.0868). These results showed that at 15-16 months, the delay 3×Tg-AD mice displayed to learn spatial information is associated with a less robust encoding than controls after a similar training regimen, and that treatment with P021 can to a certain extent successfully rescue this impairment.

As explained above in Example 1 and seen in FIG. 2, treatment with Peptide 021 did not affect general behavior in 3×Tg-AD mice. Chronic treatment with Peptide 021 in the current study did not affect the general behavioral characteristics as it neither amplified modifications of general behavior due to transgenicity nor induced new changes.

To date, there is no effective treatment or cure for tauopathies. Both in human AD cases and in various transgenic mouse models of this disease, including 3×Tg-AD mice used in the present study, neurodegeneration and loss of neuronal plasticity are known to precede Aβ and tau pathologies. Thus, an ideal drug would be one that can shift the balance from neurodegeneration to neural regeneration, inhibit tau and Aβ pathologies, and rescue cognitive impairment. The present study shows that compound P021, a neurotrophic peptide, can attenuate tau and Aβ pathologies, rescue neurogenesis and neuronal and synaptic plasticity deficits, and ameliorate cognitive impairment in 3×Tg-AD mice.

P021 is a small (mol. wt. 578.3) water-soluble compound that was administered successfully orally in diet in the present study. This CNTF derived peptidergic compound enhances DG neurogenesis and synaptic plasticity by inhibiting LIF signaling pathway and enhancing BDNF expression by increasing it's transcription. The compound has plasma half life of >3 hours and stability of >95% and >90% in artificial intestinal fluid during 2 hours and in artificial gastric juice during 30 minutes, respectively. P021 is BBB permeable and thus this small molecule mimetic overcomes the main limitation associated with therapeutic usage of neurotrophic factors such as CNTF and BDNF as peripherally administered neurotrophic factors poorly reach the central nervous system. Up to one year of administration of P021 did not show any undesirable side effects in 3×Tg-AD or control mice. Unlike recombinant CNTF, which was reported to cause anorexia, skeletal muscle loss, hyperalgesia, severe cramps, and muscle pain in humans, we did not observe any alteration in general physical state, including grooming, posture, and clasping reflex in P021-treated animals; the P021 treatment induced weight gain in these animals. The P021 treatment had no significant effect on anxiety and level of exploration in mice.

P021 is the first neurotrophic peptidergic compound that can rescue not only deficits in neurogenesis and neuronal plasticity but also robustly attenuate tau pathology and partly reduce Aβ pathology and rescue cognitive impairment in 3×Tg-AD mice at moderate to severe stages of disease. The disease-modifying effect of P021 was most likely due to induction of increase in expression of BDNF. BDNF is known to activate PI3K-AKT signaling that results in downstream inhibition of GSK-3β activity by increase in its phosphorylation at Ser9 by AKT. In the present study, an increase in BDNF expression and phosphorylation of GSK-3β at Ser9 in P021-treated 3×Tg-AD mice was found. Furthermore, in P021-treated 3×Tg-AD mice, we found a significant reduction in abnormal hyperphosphorylation of tau at several major sites some of which are known to be phosphorylated by GSK-3β in AD. The BDNF/TrkB/PI3-Kinase/GSK3β mode of action pathway of P021 on hyperphosphorylated tau in primary cultured neurons was confirmed. A significant reduction in soluble Aβ levels was found and a trend towards reduction in TS+-plaque load in P021 treated 3×TgAD mice in accordance with previous studies suggesting reduction in Aβ pathology with GSK3β inhibition. However, in the current study, it is not possible to rule out the involvement of other protein kinases or phosphatases or a direct action of P021 on APP processing in the reduction of tau and Aβ pathologies. Also, previously it has been shown that CNTF counteracts the effect of increased fibroblast growth factor-2 (FGF-2) which impairs neuronal lineage determination and maturation, resulting in promotion of neurogenesis. It has also been showed that before that FGF-2 can upregulate the expression and phosphorylation of tau by increasing the GSK3β activity. Thus, there remains a possibility that CNTF-derived P021 could be exerting its disease modifying effect in 3×Tg-AD mice by counteracting FGF-2 mediated effects.

The disease-modifying effect of P021 is also probably due to relatively long treatment, i.e., 6 to 12 months, employed in the present study. In a previous study, 6 weeks intraperitoneal administration of P6, CNTF-derived parent peptide of P021, to 6-7 month old 3×Tg-AD mice failed to show any significant effect on abnormal hyperphosphorylation of tau or intraneuronal Aβ deposition which admittedly is very little to start with in this age group of animals. Even transplantation of neuronal stem cells in 3×Tg-AD mice and BDNF gene delivery in APP+PS1 mice, both treatments that rescued synaptic plasticity deficit and cognitive impairment, failed to show any disease-modifying effect.

In the present study, P021 treatment reduced soluble but not insoluble Aβ and a trend towards reduction of Aβ plaque load was seen in CA1 but not subiculum of 3×Tg-AD mice. These findings suggest that most probably the effect of P021 on Aβ pathology was on the generation of Aβ and not its clearance after its aggregation. The plaque load was several-fold higher in subiculum than in CA1 area of hippocampus and a lesser effect of P021 treatment in the former than the latter brain region is consistent with amelioration of Aβ generation.

Age related decline in neurogenesis has been suggested to contribute to pathology leading to cognitive impairment in AD patients and in mouse models of the disease. Previously, neurotrophic and growth factors based approach has shown to have a beneficial effect on neurogenesis in animal models. Thus neurotrophic factor dependent positive enrichment of brain milieu can negate the age related decrease in neuronal proliferation and loss of new born neurons. The neurogenic effect of P021 in 3×Tg-AD mice observed in the current study further corroborates this hypothesis.

AD has been characterized as a synaptic failure. Profound synaptic loss in hippocampus in AD brains has been reported. In the present study, a significant reduction in the density of pre-synaptic marker synaptophysin, dendritic marker MAP2, and postsynaptic glutamate receptor subunits in hippocampus in 3×Tg-AD mice was observed. This dendritic and synaptic loss may lead to deficits in synaptic plasticity. It has been shown that altered basal synaptic transmission (decreased fEPSPs) and reduced LTP in 3×Tg-AD mice. Chronic treatment with P021 rescued synaptic loss. On the basis of these results, it is believed that P021 by virtue of its beneficial effect on hippocampal neurogenesis probably ameliorated the changes in homeostasis of brain milieu and provided an optimal microenvironment for neuronal proliferation and synaptogenesis, and thus enhanced synaptic plasticity.

Synaptic plasticity has been proposed to be the cellular substrate of learning and memory. The present results are consistent with the hypothesis that hippocampus dependent memory is mediated at least in part by hippocampal synaptic plasticity. Chronic treatment with P021 was found to significantly enhance two different cognitive paradigms which are known to be impaired in both AD patients and in 3×Tg-AD mice, i.e., short term memory and declarative memory modeled as spatial reference memory in mice. These findings reiterate the plastic nature of synapses and their involvement in cognition and boost the evidence of synaptic targets for therapeutic approaches in AD. Nonetheless, it's imperative to mention that the beneficial effect of P021 on cognition observed in the current study could also be due to the robust reduction in tau pathology and a mild reduction in Aβ pathology in 3×Tg-AD mice.

In the present study, chronic treatment with Peptide 021 in diet induced weight gain in WT mice. This is in contrast to previous studies with full-length CNTF protein which is reported to be anorexigenic both in human clinical trials and animal models possibly because of induction of cell proliferation in the feeding centers of the hypothalamus. Nonetheless, one study failed to find an association between CNTF and body weight in humans. CNTF has been proposed to belong to a class of cytokines that are pyrogenic; however, no significant temperature raising effect of P021 was found. Contrarily, it induced a decrease in body temperature in WT mice but had no effect on 3×Tg-AD mice.

In summary, pharmacological stimulation of neural stem cells by chronic treatment with a neurotrophic peptidergic compound not only rectified defects in neurogenesis, neuronal and synaptic plasticity, and cognition but also reduced the underlying disease pathology in 3×Tg-AD mice. This is in contrast to the more widely accepted "by stander" effect mechanism of neural stem cells, i.e., neural stem cells can improve function by providing missing or defective enzymes or modulating function or may preserve endogenous neuronal function by providing neurotrophic support. Previously, it was shown that transplantation of neuronal precursor cells (NPCs) in transgenic mice expressing human P301S tau protein exerted a neuroprotective effect by release of growth factors including CNTF and glia-derived neurotrophic factor (GDNF). Also, it has been shown that hippocampal neural stem cell transplantation improved cognition and enhanced hippocampal synaptic density via BDNF without affecting Aβ or tau pathology in 3×Tg-AD mice. However, few other studies have shown that neural stem cells or neural precursor cell implantation or enhancement of endogenous BDNF expression can have a disease modifying effect. The present invention provides further evidence that long term treatment with a CNTF peptide mimetic can attenuate tau and Aβ pathologies.

What is claimed is:

1. A method of treating a subject having a tauopathy, comprising the step of administering a therapeutic amount of a compound having the sequence Ac-DGGLAG-NH2 (SEQ ID NO: 4).

2. The method of claim 1, wherein said compound is administered peripherally.

3. The method of claim 1, wherein said compound is administered subcutaneously.

4. The method of claim 1, wherein said compound is administered orally.

5. The method of claim 1, wherein said compound is administered intraperitoneally.

* * * * *

```
                        SEQUENCE LISTING

<160> NUMBER OF SEQ ID NOS: 4

<210> SEQ ID NO 1
<211> LENGTH: 11
<212> TYPE: PRT
<213> ORGANISM: Artificial Sequence
<220> FEATURE:
<223> OTHER INFORMATION: neurotrophic and/or neurogenic peptide

<400> SEQUENCE: 1

Val Gly Asp Gly Gly Leu Phe Glu Lys Lys Leu
1               5                   10

<210> SEQ ID NO 2
<211> LENGTH: 4
<212> TYPE: PRT
<213> ORGANISM: Artificial Sequence
<220> FEATURE:
<223> OTHER INFORMATION: neurotrophic and/or neurogenic peptide

<400> SEQUENCE: 2

Asp Gly Gly Leu
1

<210> SEQ ID NO 3
<211> LENGTH: 5
<212> TYPE: PRT
<213> ORGANISM: Artificial Sequence
<220> FEATURE:
<223> OTHER INFORMATION: neurotrophic peptide exemplified with
      adamantyl-L-glycine at C-terminus

<400> SEQUENCE: 3

Asp Gly Gly Leu Gly
1               5

<210> SEQ ID NO 4
<211> LENGTH: 5
<212> TYPE: PRT
<213> ORGANISM: Artificial Sequence
<220> FEATURE:
<223> OTHER INFORMATION: neurotrophic peptide exemplified with
      adamantyl-L-glycine at C-terminus and capped at the N-terminus of
      with adamantane-1-carboxylic acid

<400> SEQUENCE: 4

Asp Gly Gly Leu Gly
1               5
```